(12) United States Patent
Chang et al.

(10) Patent No.: US 11,235,107 B2
(45) Date of Patent: Feb. 1, 2022

(54) MEDICAL INJECTION SYSTEM

(71) Applicant: SOLTEAM INCORPORATION, Taoyuan (TW)

(72) Inventors: Chun-Yun Chang, Taoyuan (TW); Yeong-Lii Lin, Taoyuan (TW); Ping-Lung Lee, Taoyuan (TW); Frederic Delort, Taoyuan (TW); Chung-Yu Chen, Taoyuan (TW)

(73) Assignee: SOLTEAM INCORPORATION, Taoyuan (TW)

( * ) Notice: Subject to any disclaimer, the term of this patent is extended or adjusted under 35 U.S.C. 154(b) by 373 days.

(21) Appl. No.: 16/519,382

(22) Filed: Jul. 23, 2019

(65) Prior Publication Data

US 2021/0023309 A1    Jan. 28, 2021

(51) Int. Cl.
*A61M 5/315* (2006.01)
*A61M 5/20* (2006.01)
*A61M 5/24* (2006.01)
*A61M 5/31* (2006.01)

(52) U.S. Cl.
CPC ...... *A61M 5/31553* (2013.01); *A61M 5/2033* (2013.01); *A61M 5/2422* (2013.01); *A61M 5/31585* (2013.01); *A61M 2005/2026* (2013.01); *A61M 2005/2418* (2013.01); *A61M 2005/2433* (2013.01); *A61M 2005/3126* (2013.01); *A61M 2205/581* (2013.01)

(58) Field of Classification Search
CPC .......... A61M 5/31553; A61M 5/31585; A61M 5/2033; A61M 5/2422; A61M 2005/2433; A61M 2005/2418; A61M 2005/3126; A61M 2205/581
See application file for complete search history.

(56) References Cited

U.S. PATENT DOCUMENTS

2007/0129687 A1* 6/2007 Marshall ................. A61M 5/20 604/207
2009/0247951 A1* 10/2009 Kohlbrenner ..... A61M 5/31553 604/134

\* cited by examiner

*Primary Examiner* — Nathan R Price
*Assistant Examiner* — Tasnim Mehjabin Ahmed
(74) *Attorney, Agent, or Firm* — ScienBiziP, P.C.

(57) ABSTRACT

A medical injection system comprising an injection module, a retract module, and a bi-directional dose setting module. The bi-directional dose setting module comprises a dose plate, and the injection module comprises a dose knob engaged with the dose plate. The medical injection system generates a first response when the dose knob is rotated in the first direction, and generates a second response when the dose knob is rotated in the second direction.

17 Claims, 29 Drawing Sheets

MEDICAL INJECTION SYSTEM

FIELD

The present disclosure generally relates to a medical injection system, particularly to a pen-shape medical injection system for drug delivery.

BACKGROUND

Medical fluids or drug can be administered to a patient by an injection system. If frequent injections of the drug are deemed necessary for the patient, then the injection system should be portable and readily operable by the patient. Therefore, a portable medical injection system is commercially available for the patient who is in need of daily injection. The portable medical injection system typically has a shape of a pen.

The patient may use the portable medical injection system to administer a particular dose of the drug. When adjusting the dose in a conventional injection pen, the patient would need to visually check the dose of the drug. It may be difficult for a visually-impaired patient to check the dose of the drug only be seeing dose marks on the conventional injection pen.

For the manufacturer of the injection system, all of the components in the injection system are assembled at the same time, and the injection systems of the same lot are subjected to an inspection of a quality control system at the same time. As there are more and more components in designs of injection systems, it is also more difficult to determine the quality of a single component when one of the lot of the injection system has failed the inspection in the quality control system. The injection system that failed the inspection would need to be dis-assemble to identify the quality issue.

Therefore, there is a need for a non-visual dose-adjustment design for the medical injection system. Also, there is a need for a modular design for the components in the injection system. Each of the module is able to be assembled and inspected separately, thus it would be easier for the manufacturer to identify quality issues if one of the module has failed quality control.

SUMMARY OF THE DISCLOSURE

In view of the shortcomings in the art, it is an objective of the present disclosure to provide a medical injection system that can be reloaded with a drug cartridge.

It is also an objective of the present disclosure to provide a medical injection system with modular designs, whereby the modules can be examined and assembled separately in the manufacturing process.

It is also an objective of the present disclosure to provide a medical injection system with a bi-directional dose setting module. The bi-directional dose setting module is capable to generate different responses when it is rotated toward different directions.

The present disclosure provides a medical injection system, comprising: an injection module, a retract module, and a bi-directional dose setting module. The injection module comprises a lead screw movable in an axial direction of the medical injection system; a driver rotatable in a first direction and configured for accommodating the lead screw, the driver comprising a resilient flange and a first engaging element, the first engaging element being on an external surface of the driver, and a shape of the driver being not identical to a shape of the lead screw along a transverse plane of the medical injection system; a fixed body comprising a ratchet and a first helical element, the ratchet being coupled to the resilient flange of the driver for preventing the driver from rotating in a second direction, and the first helical element being on an external surface of the fixed body; a dose indicia rotatable in the first direction and the second direction, the dose indicia comprising a plurality of marks and a second helical element, the plurality of marks being on an external surface of the dose indicia, and the second helical element being on the internal surface of the dose indicia and for coupling to the first helical element of the fixed body; a dose knob rotatable in the first direction and the second direction and coupled to a proximal end of the dose indicia, the dose knob comprising a plurality of first teeth and a plurality of second teeth, the first teeth being circumferentially disposed on an internal surface of the dose knob, and the second teeth facing a distal end of the medical injection system; a driver sleeve rotatable in the first direction and the second direction and partially accommodated by the fixed body, the driver sleeve being configured for partially accommodating the driver, and comprising a second engaging element and a plurality of third teeth, the second engaging element being on an internal surface of the driver sleeve and for coupling to the first engaging element of the driver, and the third teeth being capable of engaging with the first teeth of the dose knob; and a button spring disposed between the dose knob and the driver sleeve. The retract module is accommodated by the fixed body of the injection module. The bi-directional dose setting module comprises: a dose plate retainer accommodated by the dose indicia of the injection module, and comprising a lumen, a plate coupler, a proximal flange, and a distal flange, the proximal flange facing a proximal end of the medical injection system, and the distal flange facing the distal end of the medical injection system; a dose plate comprising a retainer coupler and a plurality of fourth teeth, the retainer coupler being coupled to the plate coupler, and the fourth teeth being engaged with the second teeth of the dose knob; and a dose spring disposed in the lumen and contacting the distal flange of the dose plate. Wherein when the dose knob is rotated in the first direction, the second teeth are rotated relative to the fourth teeth and a first response is generated; and when the dose knob is rotated in the second direction, the second teeth are rotated relative to the fourth teeth and a second response is generated.

According to an embodiment of the present disclosure, an amount of teeth of the second teeth is larger than an amount of teeth of the fourth teeth, each of the teeth in the fourth teeth comprises a first slope and a second slope, the first response is generated by the second teeth moving over the first slope, and the second response is generated by the second teeth moving over the second slope.

According to an embodiment of the present disclosure, an amount of teeth of the second teeth is smaller than an amount of teeth of the fourth teeth, each of the teeth in the fourth teeth comprises a first slope and a second slope, the first response is generated by the second teeth moving over the first slope, and the second response is generated by the second teeth moving over the second slope.

According to an embodiment of the present disclosure, the medical injection system further comprises a housing for accommodating the dose indicia, wherein the housing comprises a window for exposing at least one of the marks of the dose indicia.

According to an embodiment of the present disclosure, the medical injection system further comprises a cartridge module coupled to the fixed body of the injection module.

According to an embodiment of the present disclosure, the medical injection system further comprises a cap detachably coupled to the cartridge module.

According to an embodiment of the present disclosure, the medical injection system is operably configured to transform between a first state, a second state, and a third state, wherein: in the first state, the cartridge module is in contact with a retract nut of the retract module; in the second state, the button spring is relaxed, the first teeth are not engaged with the third teeth, and the driver sleeve is not rotated by a rotation of the dose knob; and in the third state, the button spring is compressed, the first teeth are engaged with the third teeth, the dose knob is rotated, the rotation of the dose knob drives the driver sleeve to rotate, the rotation of the driver sleeve drives the driver to rotate, and the rotation of the driver causes the lead screw to move axially toward the distal end of the medical injection system.

According to an embodiment of the present disclosure, the injection module further comprises a push button disposed on the proximal end of the medical injection system and coupled to the driver sleeve, and when the push button is pressed, the medical injection system is transformed from the second state to the third state.

According to an embodiment of the present disclosure, the cartridge module further comprises a stopper capable of being pushed by the lead screw when the lead screw is moved axially toward the distal end of the medical injection system.

According to an embodiment of the present disclosure, the medical injection system further comprises a cartridge module, the cartridge module comprising a holder and a cartridge, the holder being coupled to the fixed body of the injection module, and the cartridge being detachably coupled to the holder.

According to an embodiment of the present disclosure, the retract module comprises a locking nut and a retract spring, the locking nut comprises a first interconnecting element facing the distal end of the medical injection system, the retract spring is disposed between the locking nut and the retract nut, and the retract nut comprises a second interconnecting element facing the proximal end of the medical injection system.

According to an embodiment of the present disclosure, the locking nut further comprises a circular groove, and the retract spring is partially accommodated by the circular groove.

According to an embodiment of the present disclosure, the retract nut further comprises a circular groove, and the retract spring is partially accommodated by the circular groove.

According to an embodiment of the present disclosure, the medical injection system is operably configured to transform between a first state, a second state, a third state, and a fourth state, wherein: in the first state, the cartridge is in contact with the retract nut; in the second state, the button spring is relaxed, the first teeth is not engaged with the third teeth, and the driver sleeve is not rotated by a rotation of the dose knob; in the third state, the button spring is compressed, the first teeth are engaged with the third teeth, the dose knob is rotated, the rotation of the dose knob drives the driver sleeve to rotate, the rotation of the driver sleeve drives the driver to rotate, and the rotation of the driver causes the lead screw to move axially toward the distal end of the medical injection system; and in the fourth state, the cartridge is not in contact with the retract nut and the lead screw is moved axially toward the proximal end of the medical injection system.

According to an embodiment of the present disclosure, wherein when the medical injection system is in the first state, the retract spring is compressed, and the first interconnecting element and the second interconnecting element are engaged; and when the medical injection system is in the fourth state, the retract spring is relaxed, and the first interconnecting element and the second interconnecting element are not engaged.

According to an embodiment of the present disclosure, the injection module further comprises a push button disposed on the proximal end of the medical injection system and coupled to the driver sleeve, and when the push button is pressed, the medical injection system is transformed from the second state to the third state.

The present disclosure also provides another medical injection system, comprising an injection module, a retract module, and a bi-directional dose setting module. The injection module comprises a lead screw movable in an axial direction of the medical injection system; a driver rotatable in a first direction and configured for accommodating the lead screw, the driver comprising a resilient flange and a first engaging element, the first engaging element being on an external surface of the driver, and a shape of the driver being not identical to a shape of the lead screw along a transverse plane of the medical injection system; a fixed body comprising a ratchet and a first helical element, the ratchet being coupled to the resilient flange of the driver for preventing the driver from rotating in a second direction, and the first helical element being on an external surface of the fixed body; a dose adjustment element rotatable in the first direction and the second direction, the dose adjustment element comprising a plurality of marks, a second helical element, and a knob part, the plurality of marks being on an external surface of the dose adjustment element, the second helical element being on the internal surface of the dose adjustment element and for coupling to the first helical element of the fixed body, the knob part being on a proximal end of the dose adjustment element, and the knob part comprising a plurality of first teeth and a plurality of second teeth, the first teeth being circumferentially disposed in an internal surface of the knob part, and the second teeth facing a distal end of the medical injection system; a driver sleeve rotatable in the first direction and the second direction and partially accommodated by the fixed body, the driver sleeve being configured for partially accommodating the driver, and comprising a second engaging element and a plurality of third teeth, the second engaging element being on an internal surface of the driver sleeve and for coupling to the first engaging element of the driver, and the third teeth being capable of engaging with the first teeth of the knob; and a button spring disposed between the dose knob and the driver sleeve. The retract module is accommodated by the fixed body of the injection module. The bi-directional dose setting module comprises a dose plate retainer accommodated by the dose indicia of the injection module, and comprising a lumen, a plate coupler, a proximal flange, and a distal flange, the proximal flange facing a proximal end of the medical injection system, and the distal flange facing the distal end of the medical injection system; a dose plate comprising a retainer coupler and a plurality of fourth teeth, the retainer coupler coupled to the plate coupler, and the fourth teeth being engaged with the second teeth of the knob part; and a dose spring disposed in the lumen and contacting the distal flange of the dose plate. Wherein when the knob part is rotated in the first direction, the second teeth is rotated relative to the fourth teeth and a first response is generated; and when the knob part is rotated in the second direction, the second teeth are rotated relative to the fourth teeth and a second response is generated.

BRIEF DESCRIPTION OF THE DRAWINGS

The present description will be better understood from the following detailed description read in light of the accompanying drawings, where.

DETAILED DESCRIPTION

Figure 1:
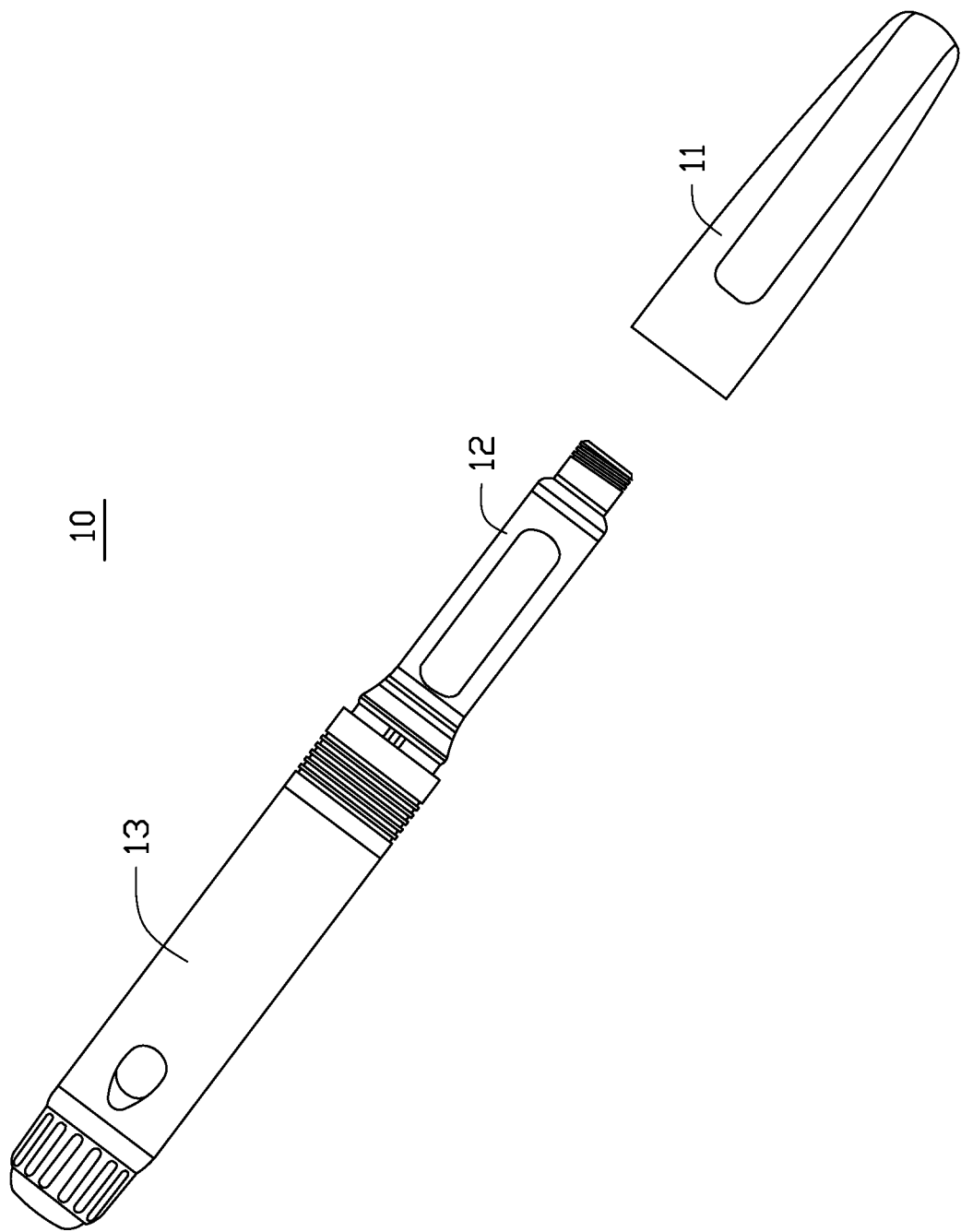
FIG. 1 is a perspective view of a medical injection system, in accordance with an embodiment of the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

The present disclosure is generally related to a medical injection system with modular designs and a reloadable cartridge structure. The term "patient" refers to an individual that can be a subject of a drug administration performed by the medical injection system of the present disclosure. The term "user" refers to an individual using the medical injection system of the present disclosure. Because the medical injection system of the present disclosure can be hold and used by the patient, so the patient and the user can be the same individual.

FIG. 1 is a perspective view of a medical injection system 10, in accordance with an embodiment of the present disclosure. A drug or a medical fluid can be administered by the medical injection system 10. The medical injection system 10 is used by the user to create a puncture on the patient's skin and administer the drug or the medical fluid. The medical injection system 10 comprises a cap 11, a cartridge module 12, and a housing 13. The cap 11 is detachably coupled to the cartridge module 12 and is disposed on a distal end of the medical injection system 10. One or all of the components in the cartridge module 12 can also be detachably coupled to the medical injection system 10 and is capable of containing the drug or the medical fluid. The housing 13 is disposed on a proximal part relative to the cartridge module 12 of the medical injection system 10. The term "distal" refers to a direction toward a puncture site of the patient's skin while using the medical injection system 10. The term "proximal" refers to another direction that is opposite to the distal direction while using the medical injection system 10. The term "axial" refers to an axis formed from the proximal end to the distal end in the medical injection system 10.

Figure 2:
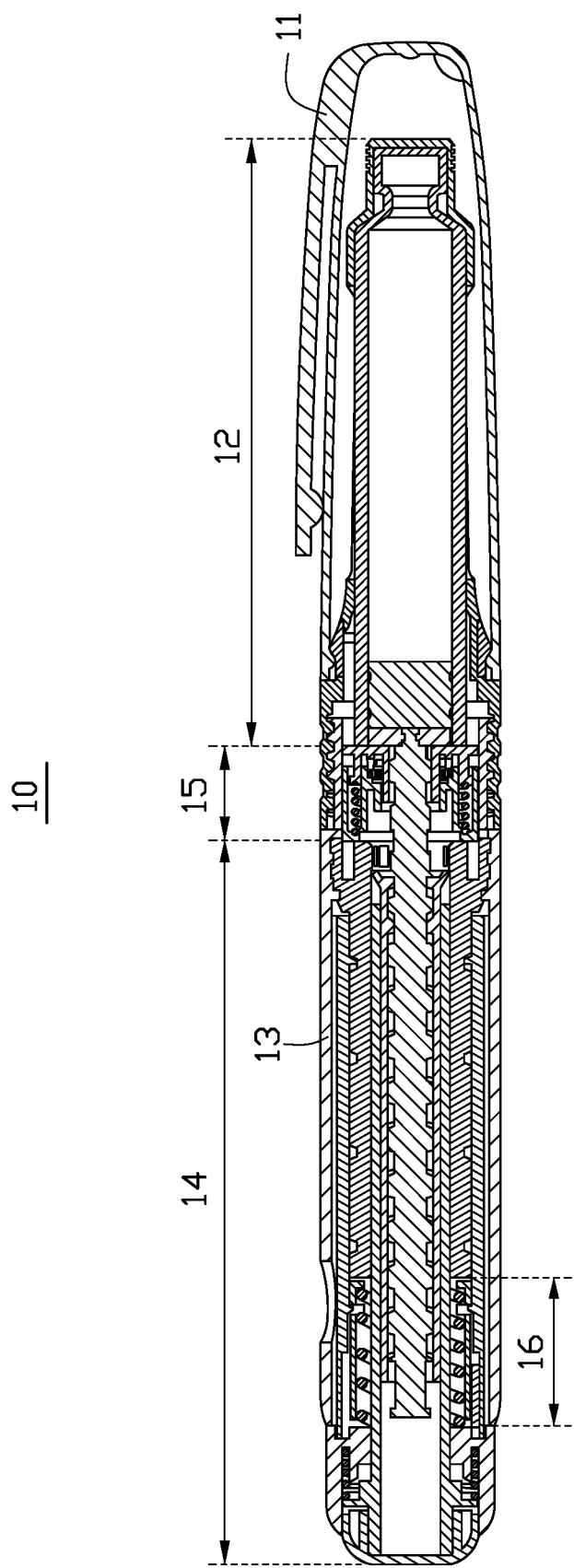
FIG. 2 is a cross-sectional view of the medical injection system, in accordance with an embodiment of the present disclosure.

FIG. 2 is a cross-sectional view of the medical injection system 10, in accordance with an embodiment of the present disclosure. The medical injection system 10 further comprises an injection module 14, a retract module 15, and a bi-directional dose setting module 16. The housing 13 accommodates some parts of the injection module 14. The injection module 14 for injecting the drug or the medical fluids is disposed on a proximal end of the medical injection system 10 and houses some parts of the bi-directional dose setting module 16. The retract module 15 is disposed between the cartridge module 12 and the injection module 14.

An objective of the present disclosure is to provide medical injection systems with modular designs, whereby the modules can be examined and assembled separately in the manufacturing process. For a manufacturer of the medical injection system 10, the cartridge module 12, the injection module 14, the retract module 15, and the bi-directional dose setting module 16 can be assembled individually. Each of the modules may be subjected to an inspection in a quality control system after it is assembled. When one of the modules does not pass the inspection, quality issues of the module can be identified individually. Thus, the manufacturer would identify the quality issue earlier and easier in the process.

Figure 3:
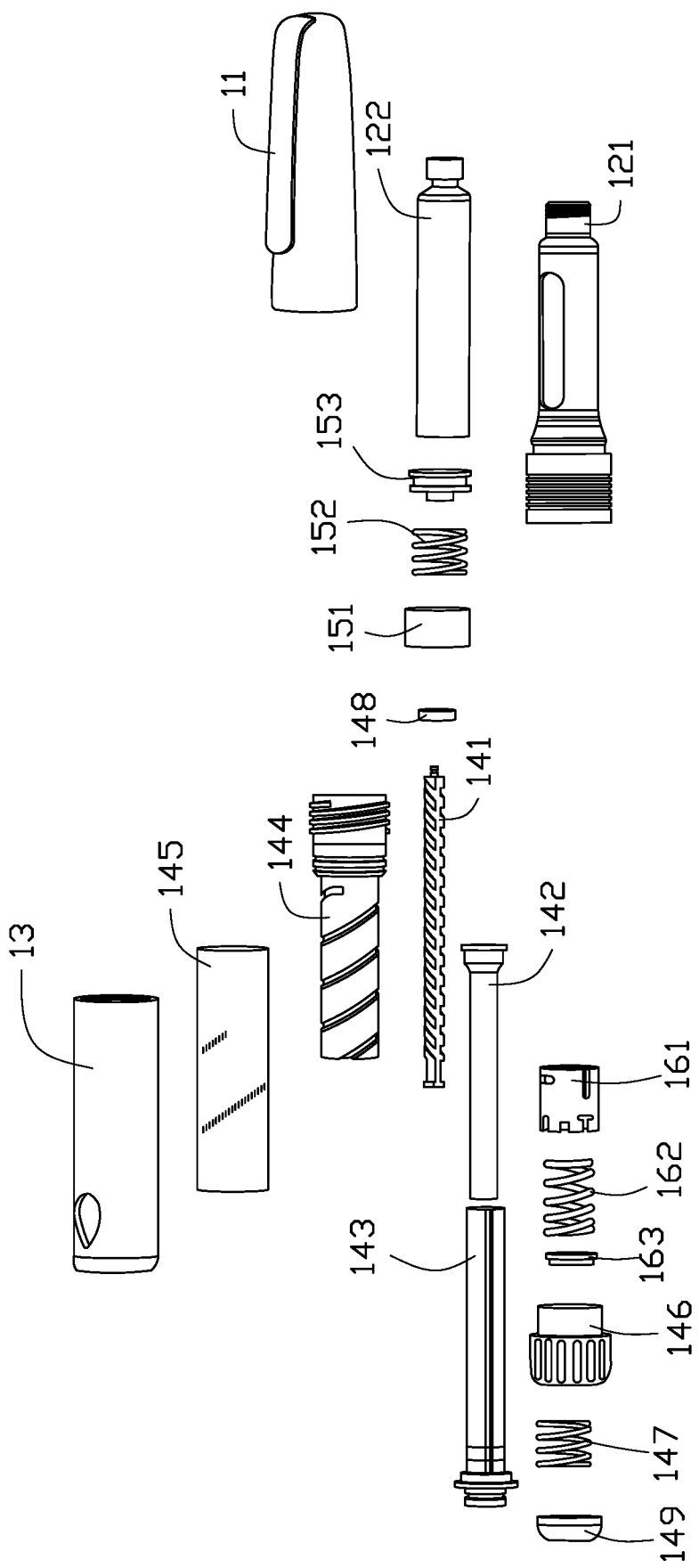
FIG. 3 is an exploded view of the medical injection system, in accordance with an embodiment of the present disclosure.

FIG. 3 is an exploded view of the medical injection system 10, in accordance with an embodiment of the present disclosure. The cartridge module 12 comprises a holder 121 and a cartridge 122. The injection module 14 comprises a lead screw 141, a driver 142, a driver sleeve 143, a fixed body 144, a dose indicia 145, a dose knob 146, a button spring 147, a rotation ring 148, and a push button 149. The retract module 15 comprises a locking nut 151, a retract spring 152, and a retract nut 153. The bi-directional dose setting module 16 comprises a dose plate retainer 161, a dose spring 162, and a dose plate 163.

Figure 4:
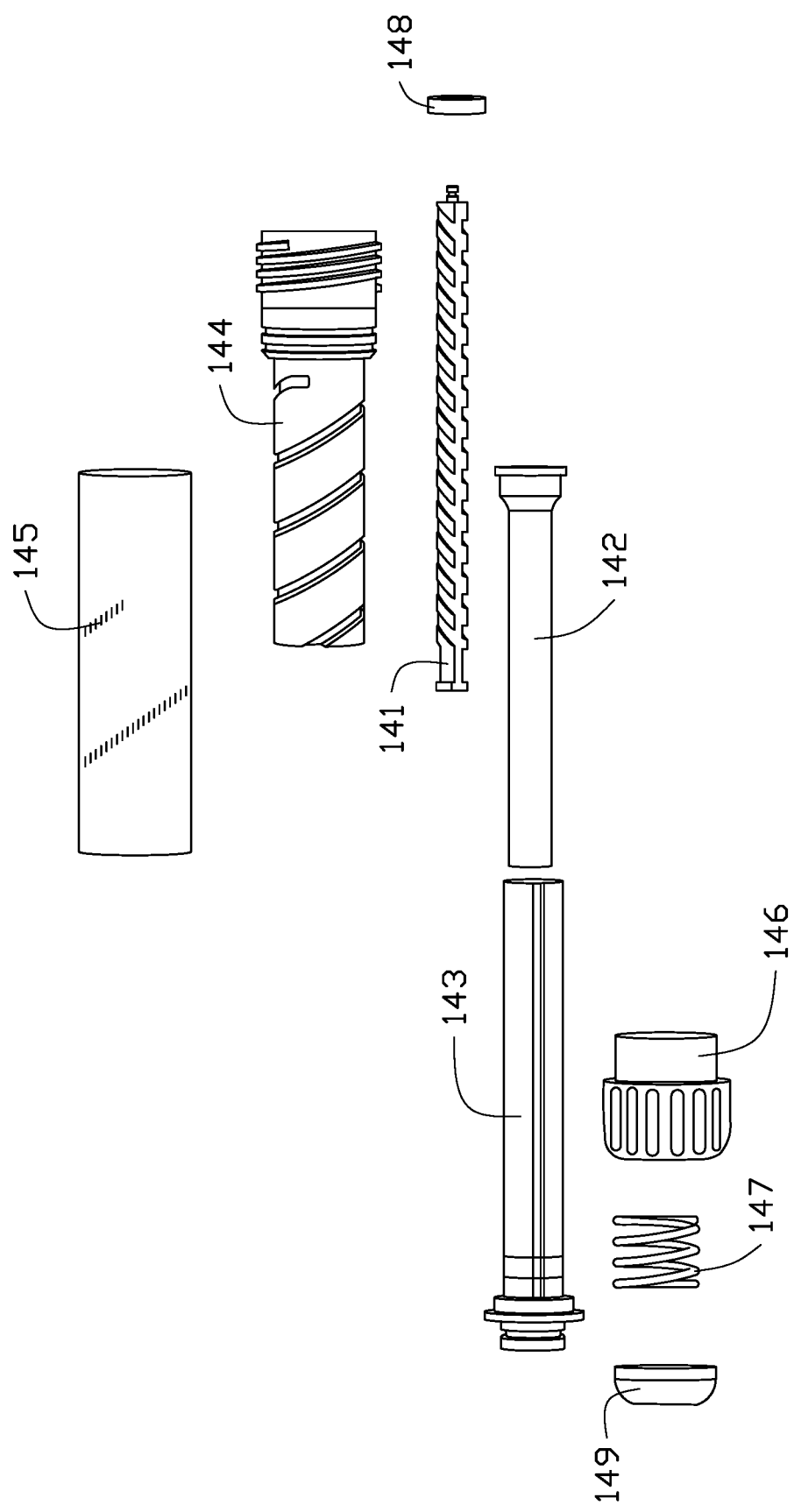
FIG. 4 is an exploded view of an injection module of the medical injection system, in accordance with an embodiment of the present disclosure.

FIG. 4 is an exploded view of the injection module 14, in accordance with an embodiment of the present disclosure. The lead screw 141, the driver 142, the driver sleeve 143, the fixed body 144, and the dose indicia 145 are generally assembled concentrically with each other, and the lead screw 141 is the innermost component among the above components. The lead screw 141 is movable in an axial direction of the medical injection system 10.

Figure 5:
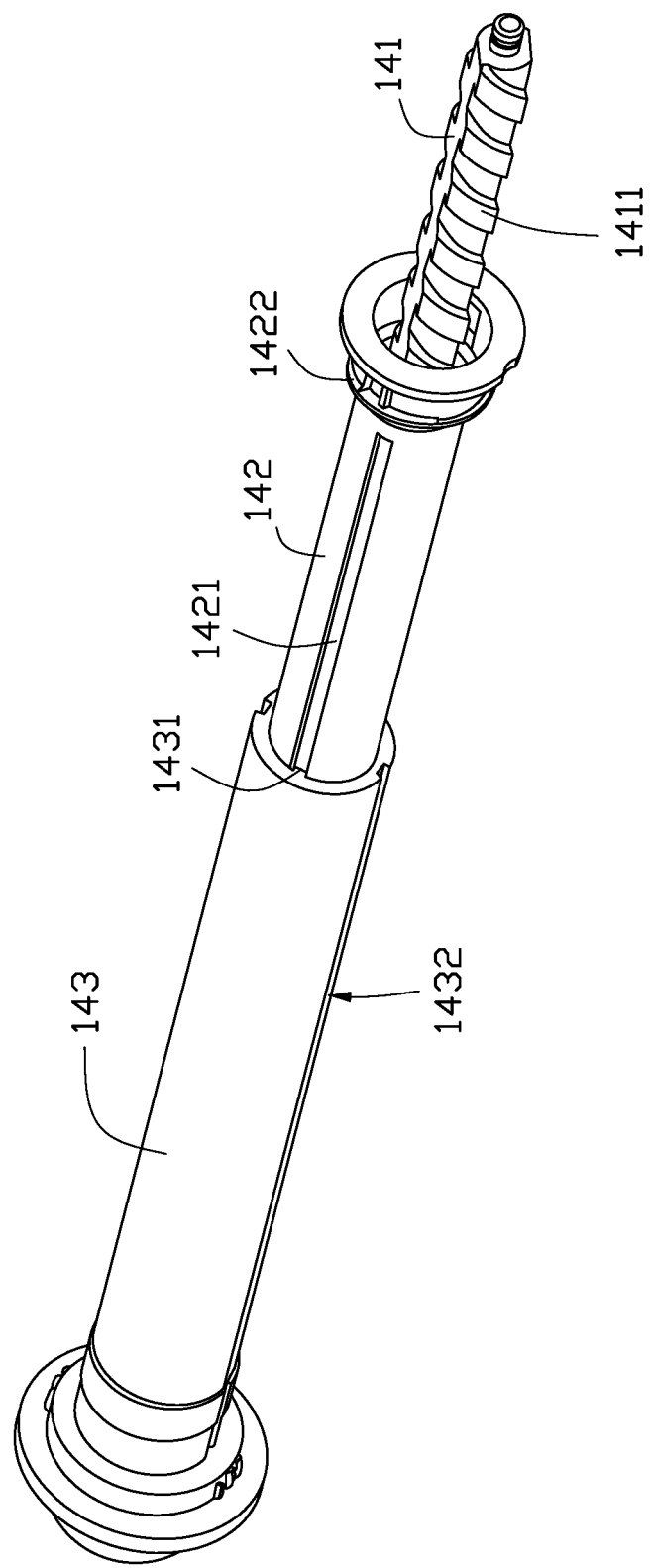
FIG. 5 is a perspective view of a lead screw, a driver, and a driver sleeve of the injection module, in accordance with an embodiment of the present disclosure.

FIG. 5 is a perspective view of a combination of the lead screw 141, the driver 142, and the driver sleeve 143, in accordance with an embodiment of the present disclosure. The distal end of the lead screw 141, the driver 142, and the driver sleeve 143 are exposed in FIG. 5. The purpose of this configuration is to illustrate how the above components are combined with each other, and the configuration is not necessarily a working status of the above components while the medical injection system 10 is hold or used by the user. The driver 142 can be a tube structure accommodating the lead screw 141 and comprising a first engaging element 1421 and a resilient flange 1422. The first engaging element 1421 is on an external surface of the lead screw 141, and the resilient flange 1422 is near the distal end of the driver 142. The first engaging element 1421 may be a longitudinal structure disposed along the axial direction of the driver 142. An opening and an internal cross-section of the driver 142 are not corresponded to a shape of the lead screw 141 along a transverse plane of the medical injection system 10. The driver sleeve 143 can also be a tube structure accommodating the driver 142, and comprising a second engaging element 1431 and a third engaging element 1432. The second engaging element 1431 is on an internal surface of the driver sleeve 143, and the third engaging element 1432 is on an external surface of the driver sleeve 143. The second engaging element 1431 may be a longitudinal structure disposed along the axial direction of the driver sleeve 143. The second engaging element 1431 of the driver sleeve 143 is coupled to the first engaging element 1421 of the driver 142. The second engaging element 1431 and the first engaging element 1421 are structurally compatible with each other: the second engaging element 1431 can be a protrusion when the first engaging element 1421 is a groove, as illustrate in FIG. 5; the second engaging element 1431 can be a groove when the first engaging element 1421 is a protrusion (not shown). The coupling between the first engaging element 1421 and the second engaging element 1431 prevents a relative rotation between the driver 142 and the driver sleeve 143.

The lead screw 141 further comprises a plurality of ribs 1411 on the external surface of the lead screw 141. The driver 142 further comprises an inner screw thread (not shown) that corresponds to the ribs 1411. When the driver 142 is rotated, the inner screw thread carries the ribs 1411, and the lead screw 141 is moved axially.

Figure 6:
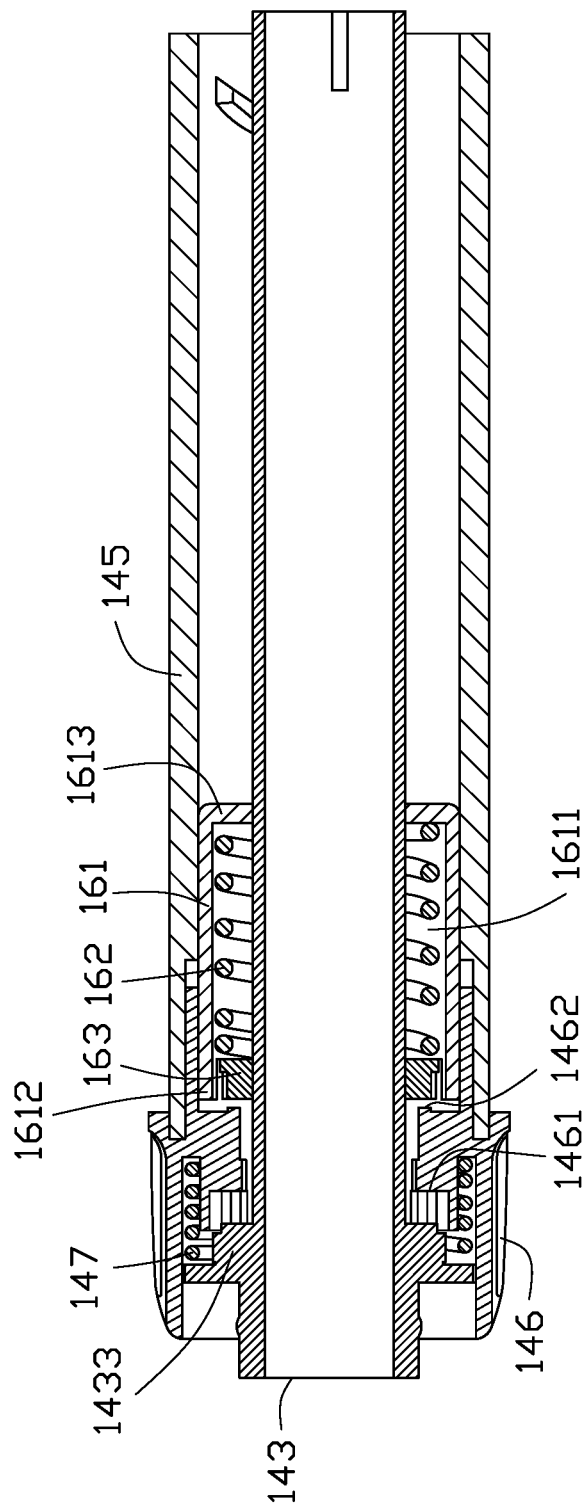
FIG. 6 is a cross-sectional view of some components of the injection module, in accordance with an embodiment of the present disclosure.

FIG. 6 is a cross-sectional view of a combination of some components of the injection module 14 and the bi-directional dose setting module 16, in accordance with an embodiment of the present disclosure. Specifically, FIG. 6 illustrates the combination of the driver sleeve 143, the dose indicia 145, the dose knob 146, the button spring 147, the dose plate retainer 161, the dose spring 162, and the dose plate 163. The injection module 14 in FIG. 6 comprises the driver sleeve 143, the dose indicia 145, the dose knob 146, and the button spring 147. The driver sleeve 143 is rotatable and further comprises a third teeth 1433 facing the distal end. The dose knob 146 is rotatable, coupled to the dose indicia 145, and comprises a plurality of a first teeth 1461 circumferentially disposed on an internal surface of the dose knob 146. The third teeth 1433 of the driver sleeve 143 is capable of engaging with the first teeth 1461 of the dose knob 146. The button spring 147 is disposed between the dose knob 146 and the driver sleeve 143. Particularly, a space for placing the button spring 147 is formed between an external side of the first teeth 1461 and the driver sleeve 143. The dose knob 146 further comprises a second teeth 1462 disposed on an opposite side of the first teeth 1461 and facing the distal end.

The bi-directional dose setting module 16 in FIG. 6 comprises the dose plate retainer 161, the dose spring 162, and the dose plate 163. The dose plate 163 is a ring-shaped structure comprising a central opening as a passage for the driver sleeve 143, and is accommodated by the dose plate retainer 161. The dose plate retainer 161 also comprises a central opening as the passage for the driver sleeve 143, a lumen 1611 for accommodating the dose spring 162, a proximal flange 1612 facing the proximal end, and a distal flange 1613 facing the distal end. The dose spring 162 is disposed in the lumen 1611 and contacted with the distal flange 1613 and the dose plate retainer 161.

Figure 7:
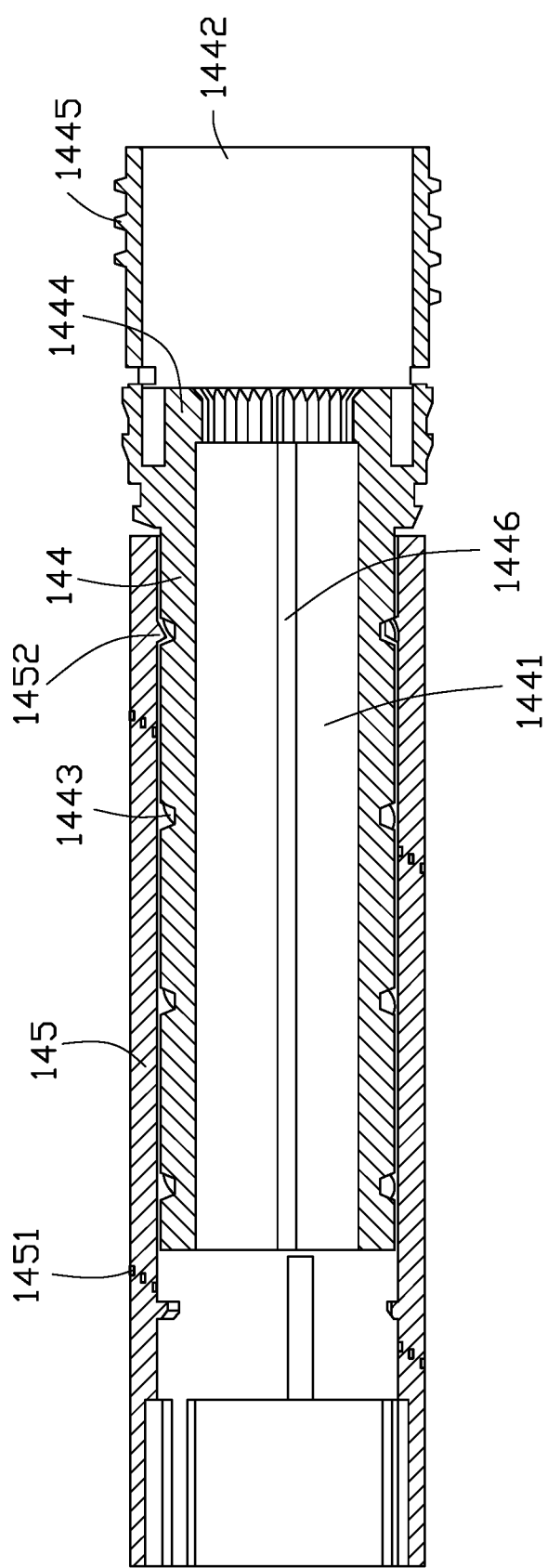
FIG. 7 is a cross-sectional view of a fixed body and a dose indicia, in accordance with an embodiment of the present disclosure.

FIG. 7 is a cross-sectional view of the fixed body 144 and the dose indicia 145, in accordance with an embodiment of the present disclosure. The fixed body 144 can be a tube structure, and comprises a first section 1441 for accommodating the driver sleeve 143 (not shown), a second section 1442 for accommodating the retract module 15 (not shown), a first helical element 1443 on an external surface of the first section 1441, a plurality of ratchets 1444 circumferentially disposed on a inner surface of the fixed body 144, a thread 1445 on the external surface of the second section 1442, and a fourth engaging element 1446 on the internal surface of the first section 1441. The first section 1441 has a smaller diameter and longer in the axial direction than the second section 1442. The first helical element 1443 is spirally disposed on the external surface of the first section 1441, as can be seen on the fixed body 144 in FIG. 3 or FIG. 4. The thread 1445 is capable to be coupled to the holder 121 when the cartridge module 12 is coupled to the medical injection system 10. The fourth engaging element 1446 of the fixed body 144 is coupled to the third engaging element 1432 of the driver sleeve 143. The fourth engaging element 1446 and the third engaging element 1432 are structurally compatible with each other, and the coupling between the fourth engaging element 1446 and the third engaging element 1432 prevents a relative rotation between the fixed body 144 and the driver sleeve 143.

The dose indicia 145 comprises a plurality of marks 1451 spirally disposed on an external surface of the dose indicia 145, and a second helical element 1452 on an internal surface of the dose indicia 145. The marks 1451 is exposed to the user when the user is using the medical injection system 10, and can be an indication of a dose of the drug or the medical fluid. The marks 1451 may have a spiral arrangement on the external surface of the dose indicia 145, as can be seen on the dose indicia 145 in FIG. 3 or FIG. 4. The second helical element 1452 corresponds to the first helical element 1443, and the second helical element 1452 can be coupled to the first helical element 1443. The second helical element 1452 can be a protrusion and the first helical element 1443 is a groove; when the second helical element 1452 is a groove, the first helical element 1443 is a protrusion.

Figure 8:
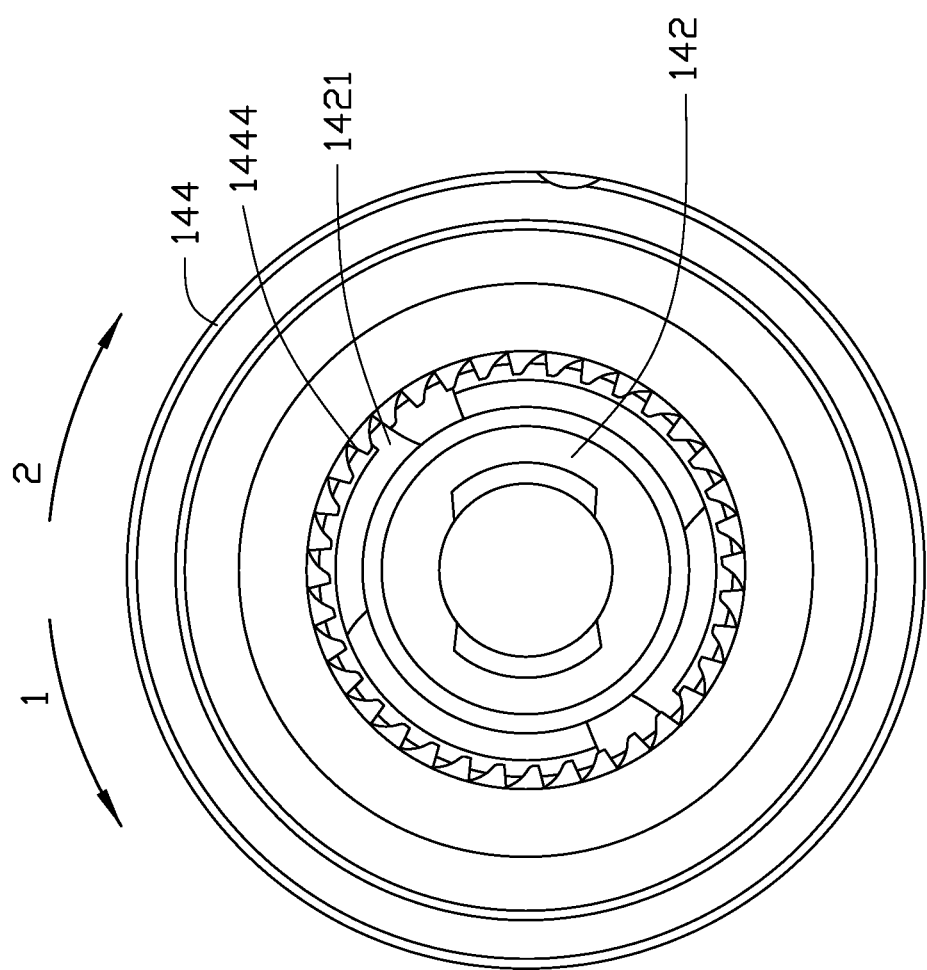
FIG. 8 is a cross-sectional view in a transverse plane of the driver and the fixed body, in accordance with an embodiment of the present disclosure.

FIG. 8 is a cross-sectional view in a transverse plane of the driver 142 and the fixed body 144, in accordance with an embodiment of the present disclosure. FIG. 8 illustrates a combination of the driver 142 and the fixed body 144 with a view point from the distal end. The ratchet 1444 of the fixed body 144 is coupled to the resilient flange 1421 of the driver 142. A plurality of teeth of the ratchet 1444 prevents the driver 142 from rotating in a second ($2^{nd}$) direction. When the resilient flange 1421 slide through the tooth of the ratchet 1444 toward a first ($1^{st}$) direction, a moderate slope of the tooth allows the resilient flange 1421 rotatable in the $1^{st}$ direction. However, when the driver 142 begins to move in the $2^{nd}$ direction, a steep slope of the tooth stops the resilient flange 1421, therefore the driver 142 would not rotate in the $2^{nd}$ direction.

With respect to the directions depicted in FIG. 8, each of the driver sleeve 143, the dose indicia 145, and the dose knob 146 are rotatable in the $1^{st}$ direction and the $2^{nd}$ direction.

Figure 9:
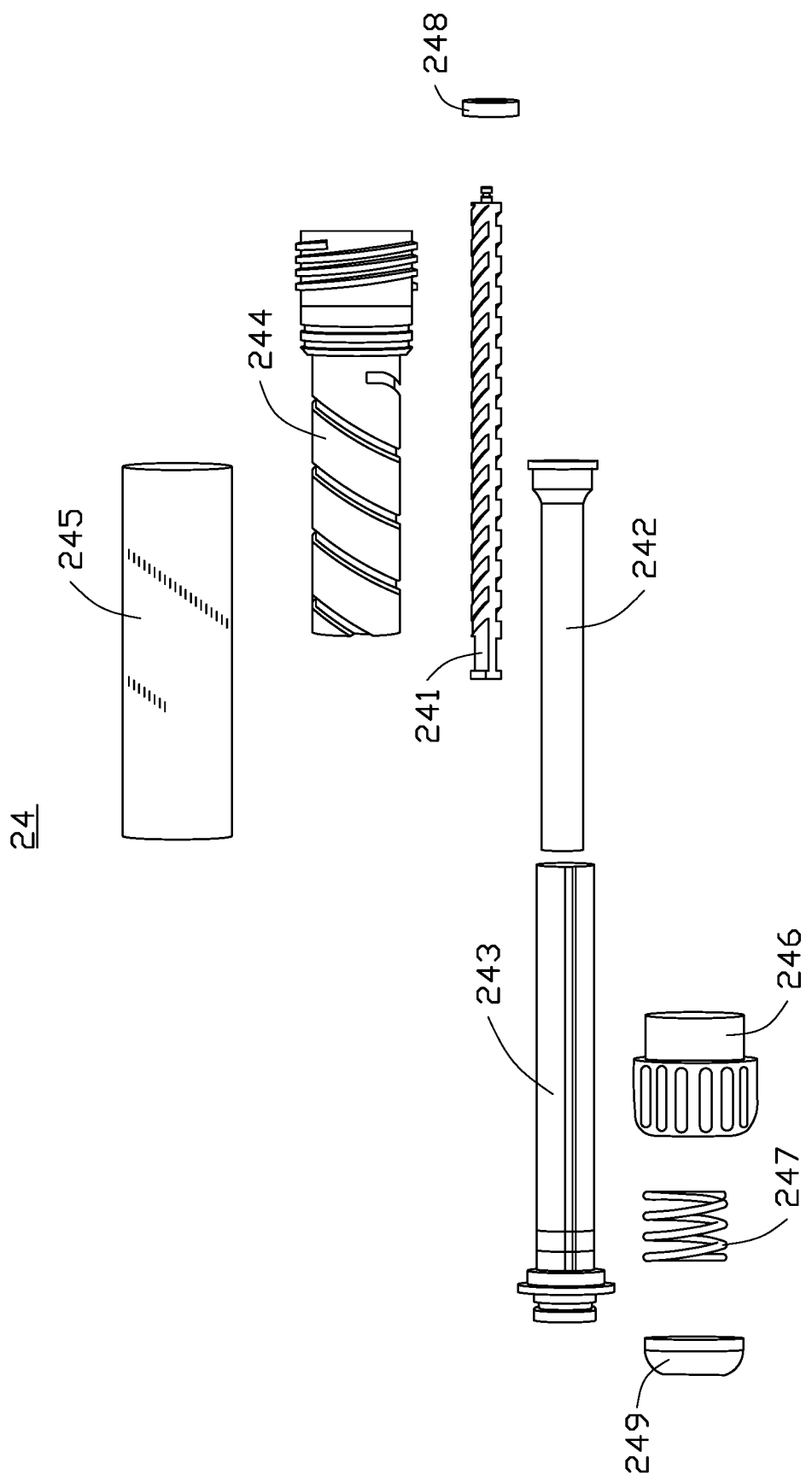
FIG. 9 is an exploded view of another injection module, in accordance with an embodiment of the present disclosure.

The $1^{st}$ direction is depicted as a counter-clockwise direction and the $2^{nd}$ direction is depicted as a clockwise direction in FIG. 8. However, for ergonomic purposes, the $1^{st}$ direction may be the clockwise direction and the $2^{nd}$ direction may be the counter-clock wise direction. FIG. 9 is an exploded view of an injection module 24, in accordance with an embodiment of the present disclosure. The injection module 24 is suitable for a left-handed user, wherein the $1^{st}$ direction is the clockwise direction and the $2^{nd}$ direction is the counter-clockwise direction. The injection module 24 comprises a lead screw 241, a driver 242, a driver sleeve 243, a fixed body 244, a dose indicia 245, a dose knob 246, a button spring 247, a rotation ring 248, and a push button 249. The fixed body 244 comprises a first helical element 2441 on an external surface of the fixed body 244, and the first helical element 2441 spirals toward an opposite direction with the first helical element 1443. The dose indicia 245 comprises a second helical element (not shown) in an internal surface of the dose indicia 245, the second helical element corresponds to the first helical element 2441. The second helical element of the dose indicia 245 also spirals toward an opposite direction with respect to the second helical element 1452 of the injection module 14.

Figure 10:
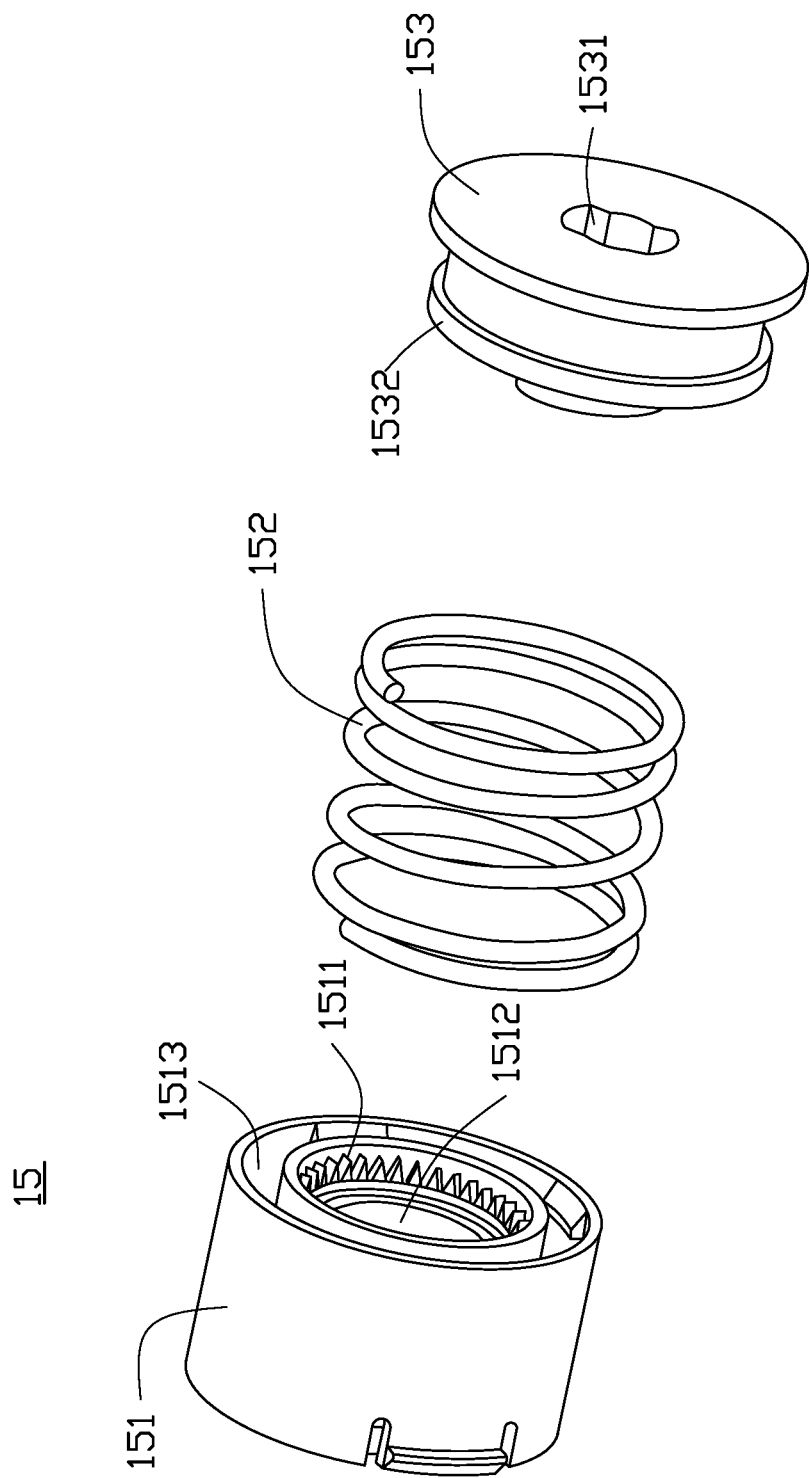
FIG. 10 is an exploded view of a retract module of the medical injection system, in accordance with an embodiment of the present disclosure.

FIG. 10 is an exploded view of the retract module 15, in accordance with an embodiment of the present disclosure. The locking nut 151 comprises a first interconnecting element 1511 facing the distal end of the locking nut 151, a first opening 1512 capable of being passed through by the lead screw 141, and a locking groove 1513. The first interconnecting element 1511 can be a circular arrangement of teeth around the first opening 1512. The retract nut 153 comprises a second opening 1531 also being capable of being passed through by the lead screw 141 and a retract flange 1532. The second opening 1531 can be smaller than the first opening 1512, and the second opening 1531 has a shape corresponding to the shape of the lead screw 141 in the transverse plane of the medical injection system 10. The retract flange 1532 is inserted in the locking groove 1513, and the retract spring 152 is disposed in the locking groove 1513 of the locking nut 151 and abutted against the retract flange 1532 of the retract nut 153. The locking groove 1513 is circular and can be concentrically located outside of the first interconnecting element 1511.

Figure 11:
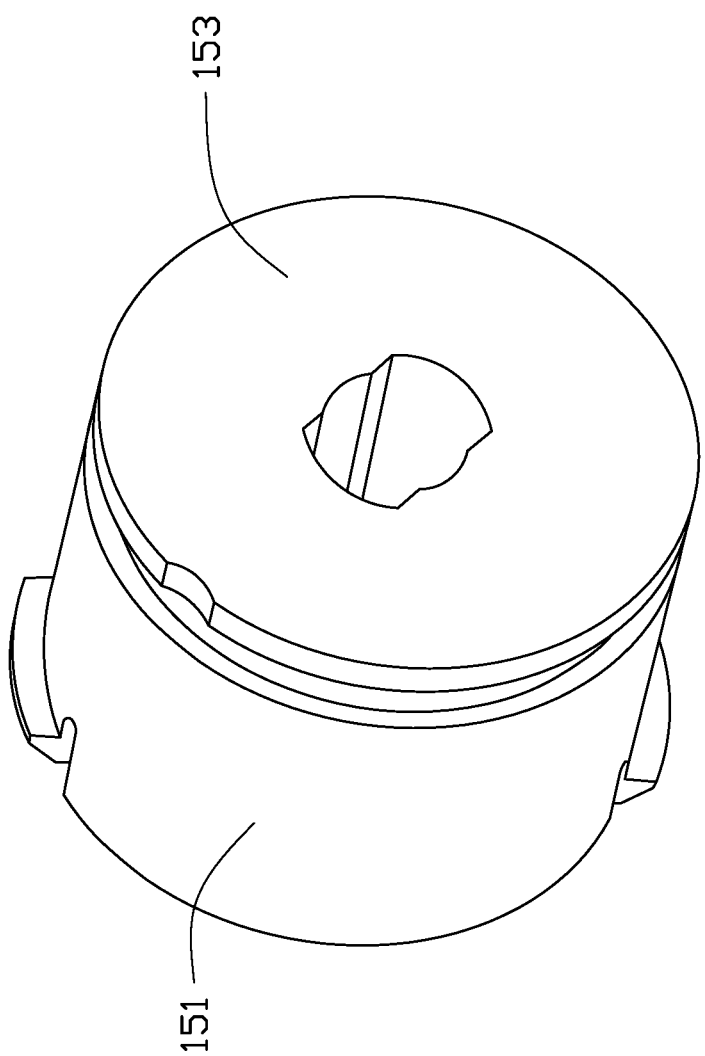
FIG. 11 is a perspective view of a retract nut and a locking nut, in accordance with an embodiment of the present disclosure.

FIG. 11 is a perspective view of a combination of the locking nut 151 and the retract nut 153, in accordance with an embodiment of the present disclosure. FIG. 10 illustrates the combination with the view point from the distal end. In FIG. 10, the retract nut 153 is facing the distal end, and the second opening 1531 can be seen from the distal end.

Figure 12A:
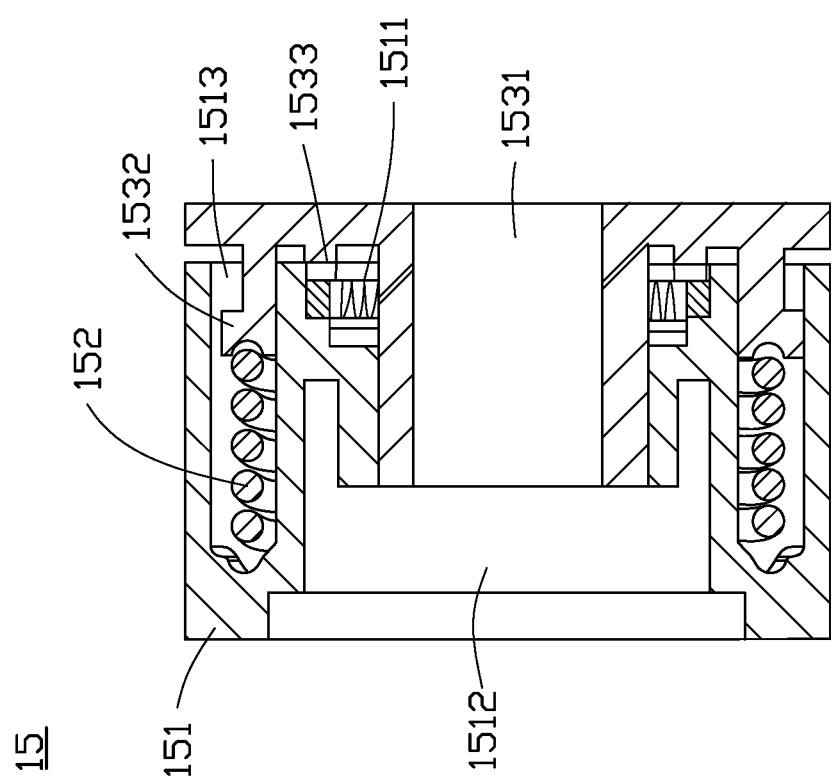
FIG. 12A is a cross-sectional view of the retract module, in accordance with an embodiment of the present disclosure.

FIG. 12A is a cross-sectional view of the retract module 15, in accordance with an embodiment of the present disclosure. The retract spring 152 is disposed between the locking nut 151 and the retract nut 153. Specifically, the retract spring 152 is disposed in a space formed between the locking groove 1513 and the retract flange 1532. A second interconnecting element 1533 of the retract nut 153 is disposed around the second opening 1531, and the second interconnecting element 1533 is facing the proximal end. The second interconnecting element 1533 can be a circular arrangement of teeth around the second opening 1531, and the locking flange 1532 can be concentrically located outside of the second interconnecting element 1533. FIG. 12A illustrates the retract module 15 in a $1^{st}$ state of the medical injection system 10: when the retract spring 152 is compressed, the first interconnecting element 1511 of the locking nut 151 and the second interconnecting element 1533 of the retract nut 153 are engaged. Therefore, a relative rotation between the locking nut 151 and the retract nut 153 is prevented. The compression of the retract spring 152 is caused by the retract nut 153, and the retract nut 153 is moved by a movement of another component or module in the medical injection system 10.

Figure 12B:
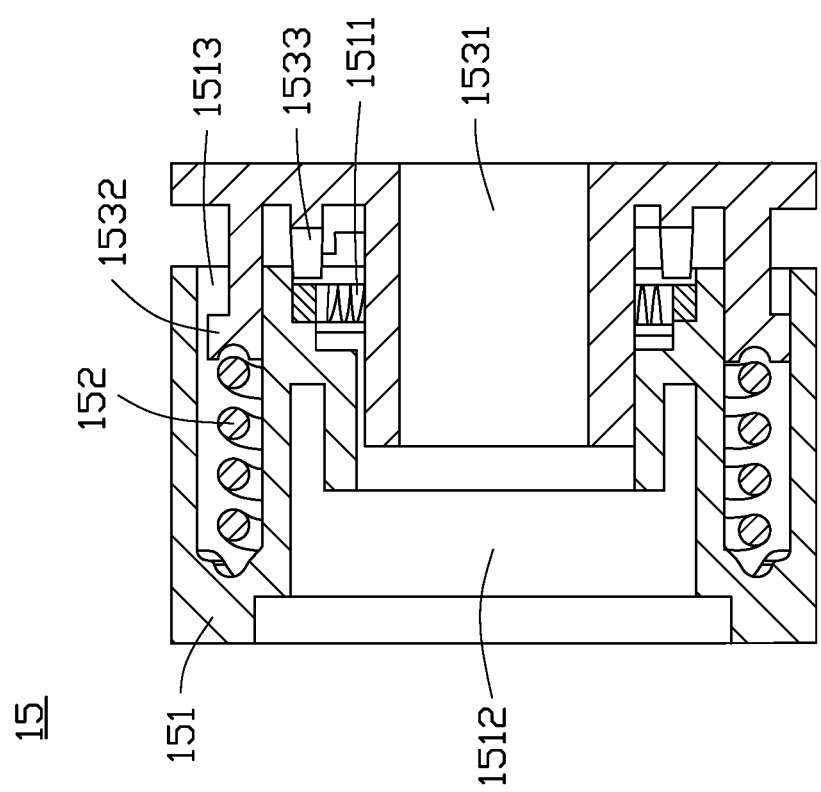
FIG. 12B is another cross-sectional view of the retract module, in accordance with an embodiment of the present disclosure.

FIG. 12B is another cross-sectional view of the retract module 15, in accordance with an embodiment of the present disclosure. FIG. 12B illustrates the retract module 15 in a fourth ($4^{th}$) state of the medical injection system 10: when the retract spring 152 is relaxed, the first interconnecting element 1511 of the locking nut 151 and the second interconnecting element 1533 of the retract nut 153 are not engaged. Therefore, a relative rotation between the locking nut 151 and the retract nut 153 is possible.

The transition between from the $4^{th}$ state to the $1^{st}$ state is caused by the cartridge 122 being loaded into the medical injection system 10. Specifically, the cartridge 122 is in contact with the react nut 153. This combination of the cartridge 122 and the retract nut 153 causes an axial movement of the retract nut 153 toward the proximal end. Then the retract spring 152 is compressed by the axial movement.

Figure 13:
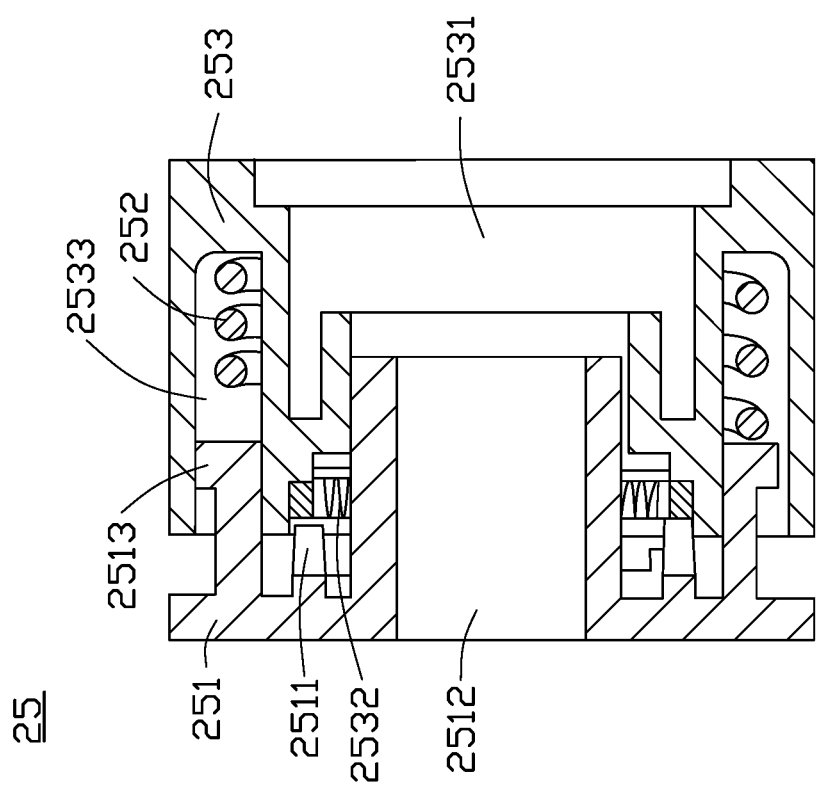
FIG. 13 is a cross-sectional view of another retract module, in accordance with an embodiment of the present disclosure.

FIG. 13 is a cross-sectional view of another retract module, in accordance with an embodiment of the present disclosure. In FIG. 12, the proximal end is the left side of figure and the distal end is the right side of the figure. A retract nut 25 is provided by an embodiment of the present disclosure. The retract nut 25 comprises a locking nut 251, a retract spring 252, and a retract nut 253. The locking nut 251 comprises a first interconnecting element 2511 facing the distal end, a first opening 2512, and a locking flange 2513 protruding toward the distal end. The first interconnecting element 2511 can be a circular arrangement of teeth around the first opening 2512, and the locking flange 2513 can be concentrically located outside of the first interconnecting element 2511. The first opening 2512 can be passed through by a lead screw (not shown). The retract nut 253 comprises a second opening 2531, a second interconnecting element 2532 facing the proximal end, and a retract groove 2533. The second interconnecting element 2532 can be a circular arrangement of teeth around the second opening 2531, and the retract groove 2533 is circular and can be concentrically located outside of the second interconnecting element 2532. The locking flange 2513 is inserted in the retract groove 2533. The retract spring 252 is disposed in the retract groove 2533 of the retract nut 253, and the retract spring 252 is abutted against the locking flange 2513 of the locking nut 251.

The retract module 25 can be in a $1^{st}$ state wherein the retract spring 252 is compressed, and a $4^{th}$ state wherein the retract spring 252 is relaxed. Similar to the compression and relaxation of the retract spring 152 in the retract module 15, a compression the retract spring 252 in the retract module 25 is caused by the retract nut 253. The retract nut 253 may be moved by a movement of another component or module.

Figure 14A:
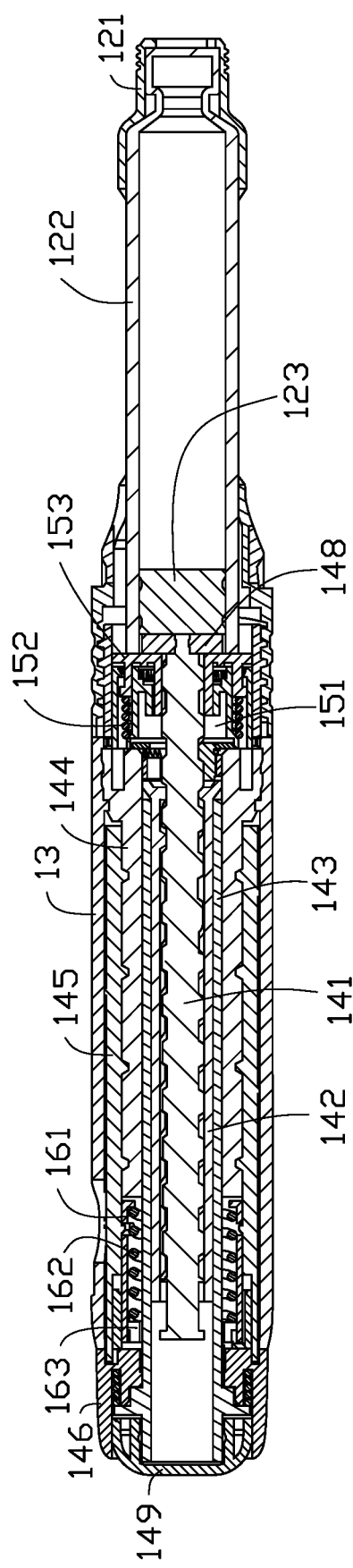
FIG. 14A is a cross-sectional view of a first ($1^{st}$) state of the medical injection system, in accordance with an embodiment of the present disclosure.

FIG. 14A is a cross-sectional view of the $1^{st}$ state of the medical injection system 10, in accordance with an embodiment of the present disclosure. In FIG. 14A, the cartridge module 12 is in contact with the retract nut 153. The holder 121 of the cartridge module 12 is coupled to the fixed body 144, the retract nut 153 is abutted against the cartridge 122, and the retract nut 153 is moved axially. The lead screw 141 passes through the first opening 1512 of the locking nut 151 and the second opening 1531 of the retract nut 153. The distal end of the lead screw 141 is coupled to the rotation ring 148, and a stopper 123 of the cartridge module 12 is in contact with the lead screw 141 and the rotation ring 148.

Some components in the injection module 14 in the $1^{st}$ state are also shown in FIG. 14A. The lead screw 141 is partially accommodated by the driver 142. The driver 142 is at least partially accommodated by the driver sleeve 143. The driver sleeve 143 is accommodated by the first section 1441 of the fixed body 144. The fixed body 144 is partially accommodated by the dose indicia 145. The bi-directional dose setting module 16 is also accommodated by the dose indicia 145. The dose indicia 145 is partially accommodated by the housing 13. The lead screw 141, the driver 142, the driver sleeve 143, the fixed body 144, the dose indicia 145, and the housing 13 are assembled concentrically. The dose knob 146 is coupled to the proximal end of the dose indicia 145. The push button 149 is disposed on the proximal end of the injection module 14 and coupled to the driver sleeve 143.

The holder 121 of the cartridge module 12 can be detachably coupled to an external surface of the second section 1442 of the fixed body 144, and the cartridge 122 is fixed by the holder 121. The drug or the medical fluid is contained in the cartridge 122. When the holder 121 is coupled to the fixed body, the cartridge 122 can be detachably coupled to the holder 121, and the cartridge 122 can be loaded to the cartridge module 12. The stopper 123 is disposed in the cartridge 122 for being pushed by the injection module 14 and defining a volume of the drug or the medical fluid contained in the cartridge 122. A hollow needle (not shown) for puncturing the skin of the patient can be coupled to the holder 121, for delivering the drug or the medical fluid contained in the cartridge 122.

Figure 14B:
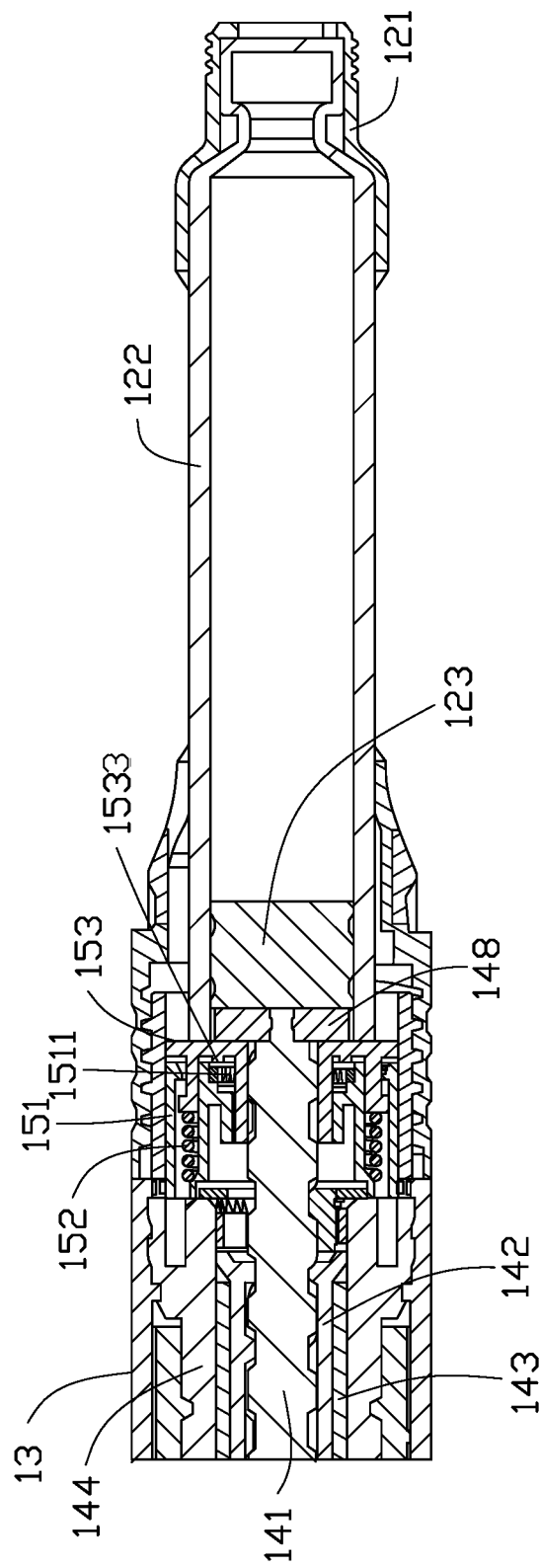
FIG. 14B is another cross-sectional view of the $1^{st}$ state of the medical injection system, in accordance with an embodiment of the present disclosure.

FIG. 14B is another cross-sectional view of the $1^{st}$ state of the medical injection system 10, in accordance with an embodiment of the present disclosure. FIG. 14B is a partially enlarged version of FIG. 14A. When the cartridge 122 is loaded, particularly the cartridge 122 is in contact with the retract nut 153, the retract nut 153 is pushed by the cartridge 122, thereby the retract spring 152 is compressed. The first interconnecting element 1511 of the locking nut 151 and the second interconnecting element 1533 of the retract nut 153 are engaged. The driver 142 can be rotated in the $1^{st}$ direction to move the lead screw 141 toward the distal end in the axial direction of the medical injection system 10.

Figure 15A:
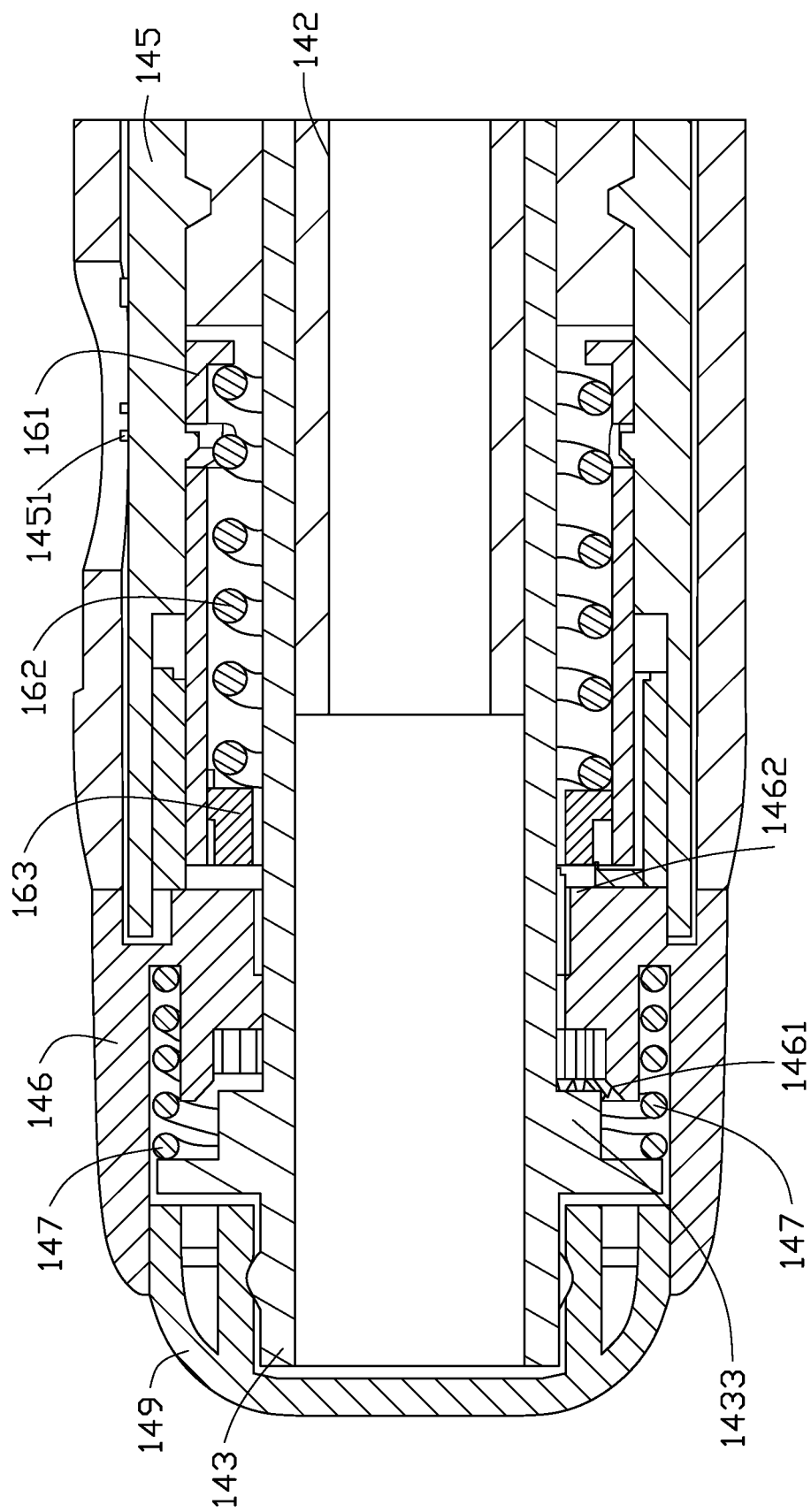
FIG. 15A is a cross-sectional view of a second ($2^{nd}$) state of the medical injection system, in accordance with an embodiment of the present disclosure.

FIG. 15A is a cross-sectional view of a part of the medical injection system 10, in accordance with an embodiment of the present disclosure. In FIG. 15A, the medical injection system 10 is in a $2^{nd}$ state: the button spring 147 is relaxed, and the first teeth 1461 of the dose knob 146 is not engaged with the third teeth 1433 of the driver sleeve 143. Because the first teeth 1461 is not engaged with the third teeth 1433, therefore the rotation of the dose knob 146 does not affect the driver sleeve 143. The dose knob 146 can be rotated by the user, and the dose indicia 145 coupled to the dose knob 146 is also rotated. Therefore, the user may rotate the dose knob 146 to cause the rotation of the dose indicia 145, and the marks 1451 indicates the dose during the rotation. The user may adjust the dose of the drug or the medical fluids according to the marks 1451.

Figure 15B:
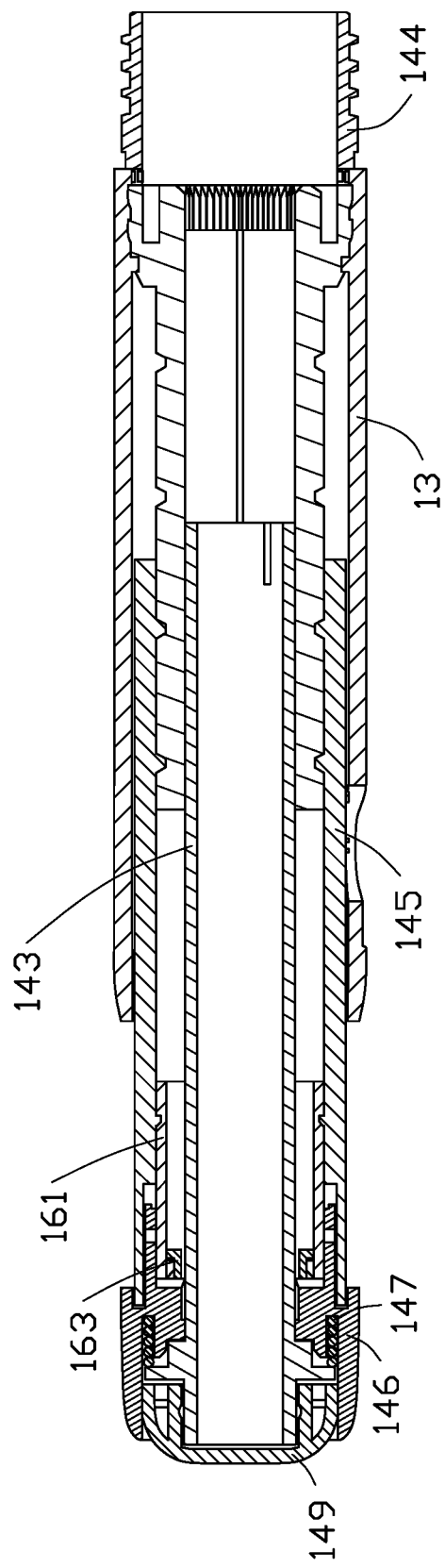
FIG. 15B is another cross-sectional view of the $2^{nd}$ state of the medical injection system, in accordance with an embodiment of the present disclosure.

FIG. 15B is another cross-sectional view of the $2^{nd}$ state of the medical injection system 10, in accordance with an embodiment of the present disclosure. In FIG. 15B, the push button 149, the button spring 147, the dose knob 146, the driver sleeve 143, and the dose indicia 145 are moved axially toward the proximal end, and a part of the dose indicia 145 is not covered by the housing 13. Because the button spring 147 is abutted against the driver sleeve 143, the driver sleeve 143 is pushed toward the proximal end by the axial movement of the button spring 147.

Figure 16:
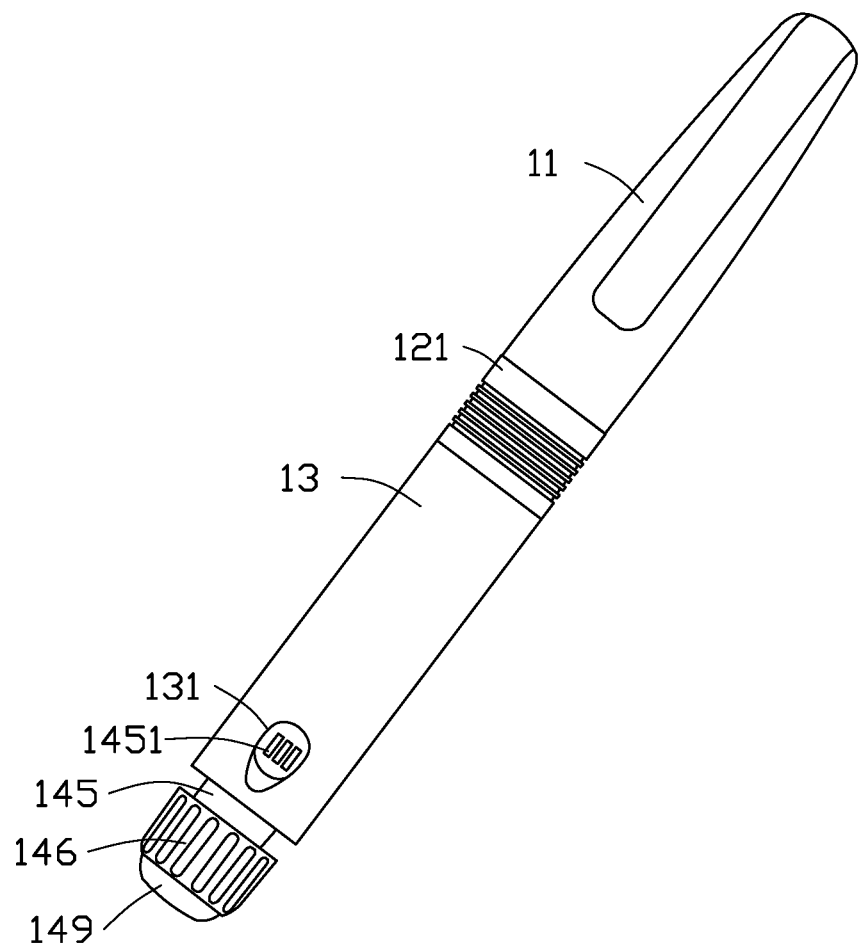
FIG. 16 is a perspective view of the $2^{nd}$ state of the medical injection system, in accordance with an embodiment of the present disclosure.

FIG. 16 is a perspective view of FIG. 15B, in accordance with an embodiment of the present disclosure. When adjusting the dose, the dose knob 146 may be rotated toward the $1^{st}$ direction, and the dose indicia 145 is also rotated toward the $1^{st}$ direction. A relative rotation between the dose indicia 145 and the fixed body 144 is generated because of the coupling between the second helical element 1452 and the first helical element 1443. The rotation toward the $1^{st}$ direction exposes an area of the external surface of the dose indicia 145, whereby the area is not covered by the housing 13.

The housing 13 comprises a window 131 exposing one of the marks 1451. The dose of the drug or the medical fluid is indicated by one of the marks 1451 that is seen from the window 131. The marks 1451 that can be seen from the window 131 may be switched from one mark to another mark while the dose knob 146 is rotated.

The dose knob 146 may be rotated toward the $2^{nd}$ direction, and the dose indicia 145 is also rotated toward the $2^{nd}$ direction. The rotation toward the $2^{nd}$ direction decreases the exposed area on the external surface of the dose indicia 145, and increases an area of the external surface of the dose indicia 145 that is covered by the housing 13.

Figure 17:
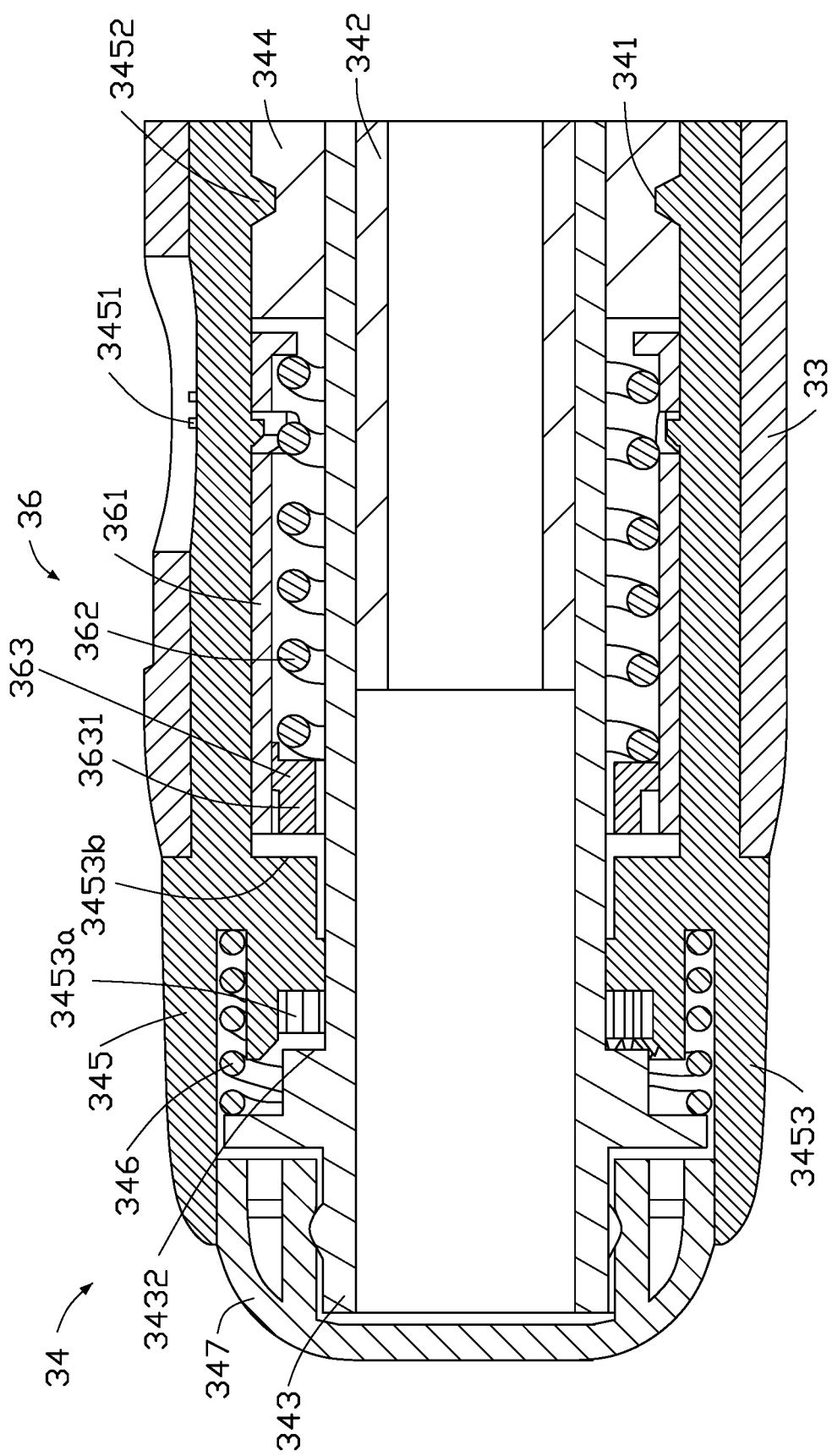
FIG. 17 is a cross-sectional view of a part of another injection module and another bi-directional dose setting module, in accordance with an embodiment of the present disclosure.

Because the dose knob and the dose indicia in the embodiment are coupled for dose adjustment, they could be an integral piece to perform dose adjustment. FIG. 17 is a cross-sectional view of a part of another injection module 34 and another bi-directional dose setting module 36, in accordance with an embodiment of the present disclosure. The injection module 34 comprises a driver 342, a driver sleeve 343, a fixed body 344, a dose adjustment element 345, a button spring 346, and a push button 347. The driver 342 is accommodated by the driver sleeve 343. The driver sleeve 343 is partially accommodated by the fixed body 344. The button spring 346 is disposed between the dose adjustment element 345 and the driver sleeve 343. The push button is disposed on a distal end of the injection module 34. The dose adjustment element 345 is rotatable in the $1^{st}$ direction and the $2^{nd}$ direction, and comprises a plurality of marks 3451, a second helical element 3452, and a knob part 3453. The marks are on an external surface of the dose adjustment element 345. The second helical element 3452 is on the internal surface of the dose adjustment element 345, and the second helical element 3452 is coupled to a first helical element 3441 on an external surface of a fixed body 344. The knob part 3453 is on a proximal end of the dose adjustment element 345, and comprises a plurality of first teeth 3453a and a plurality of second teeth 3453b. The first teeth 3453a is circumferentially disposed in an internal surface of the knob part 3453, and the second teeth 3453b is facing a distal end of the injection module 34, or a distal end of the medical injection system 34 (not fully shown). The first teeth 3453a could engage with a third teeth 3432 of the driver sleeve 343.

The bi-directional dose setting module 36 comprises a dose plate retainer 361, a dose spring 362, and a dose plate 363. The dose plate retainer 361 is accommodated by the dose adjustment element 345, and comprises a lumen. The dose plate 363 is disposed within the dose plate retainer 361, and comprises a plurality of fourth teeth 3631 facing a proximal end of the bi-directional dose setting module 36. The dose spring 362 is disposed in the lumen of the dose plate retainer 361 and is in contact with the dose plate 363. The fourth teeth 3631 of the dose plate 363 could engage with the second teeth 3453b of the knob part 3453.

Figure 18A:
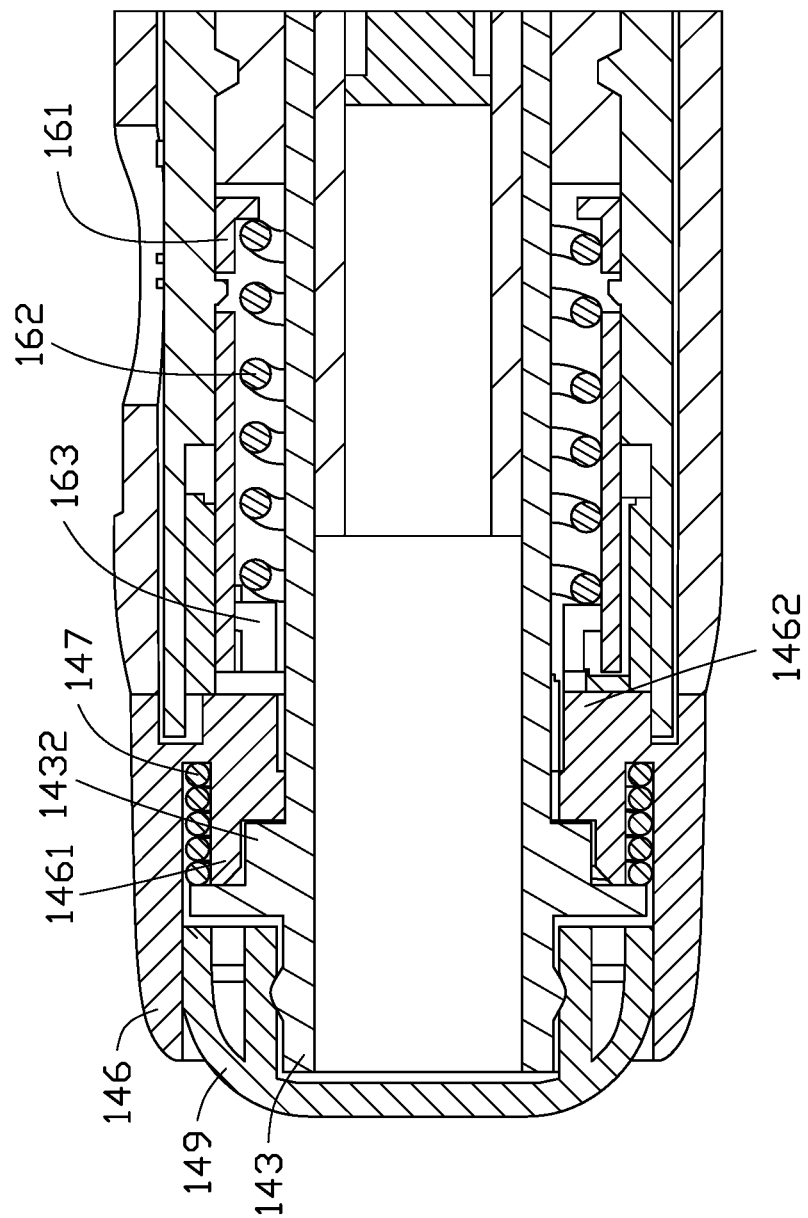
FIG. 18A is a cross-sectional view of a third ($3^{rd}$) state of the medical injection system, in accordance with an embodiment of the present disclosure.

FIG. 18A is another cross-sectional view of a part of the medical injection system 10, in accordance with an embodiment of the present disclosure. In FIG. 18A, the medical injection system 10 is in a third ($3^{rd}$) state: the button spring 147 is compressed, the first teeth 1461 of the dose knob 146 is engaged with the third teeth 1433 of the driver sleeve 143. Because the dose knob 146 is engaged with the driver sleeve 143, therefore the driver sleeve 143 can be rotated with the dose knob 146. In the $3^{rd}$ state, the components directly coupled to the dose knob 146 would be rotated when the dose knob 146 is rotated: the driver sleeve 143 and the dose indicia 145 are such components. The compression of the button spring 147 is caused by the push button 149. The push button 149 can be pressed by the user to trigger an axial movement of the driver sleeve 143 toward the distal end. The push button 149 is pressed to transform the medical injection system 10 from the $2^{nd}$ state to the $3^{rd}$ state.

Figure 18B:
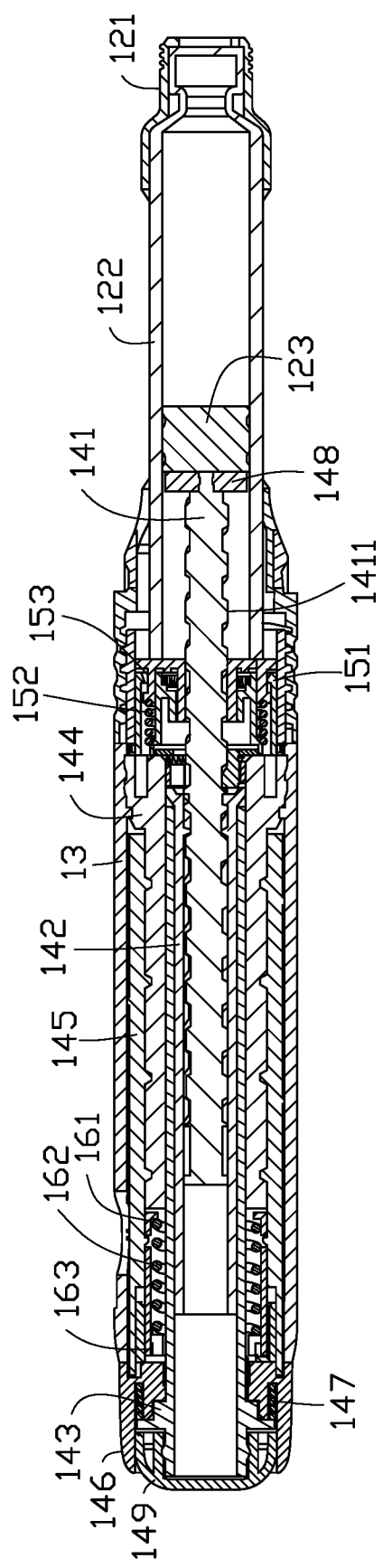
FIG. 18B is another cross-sectional view of the $3^{rd}$ state of the medical injection system, in accordance with an embodiment of the present disclosure.

FIG. 18B is a cross-sectional view of the medical injection system 10 in the $3^{rd}$ state, in accordance with an embodiment of the present disclosure. A push from the push button 149 drives the driver sleeve 143 and the dose knob 146 to rotate and to move axially. The rotation of the dose knob 146 drives the driver sleeve 143 to rotate, and the rotation of the driver sleeve 143 drives the driver 142 to rotate. The rotation of the driver 142 and the driver sleeve 143 are accompanied by axial movements of the driver 142 and the driver sleeve 143. The axial movement of the driver 142 is transformed onto the inner screw thread of the driver 142, and the lead screw 141 is moved axially due to a combination of the ribs 1411 and the inner screw thread. The rotation of the driver 142 causes the lead screw 141 to move axially toward the distal end. The opening and the internal cross-section of the driver 142 are not corresponded to the shape of the lead screw 141 in the transverse plane, therefore, the lead screw 141 is not rotated when it is moved axially. The stopper 123 disposed in the cartridge 122 is pushed by the lead screw 141 and the rotation ring 148. Then, the drug or the medical fluid contained in the cartridge 122 is administered to the patient.

Figure 19A:
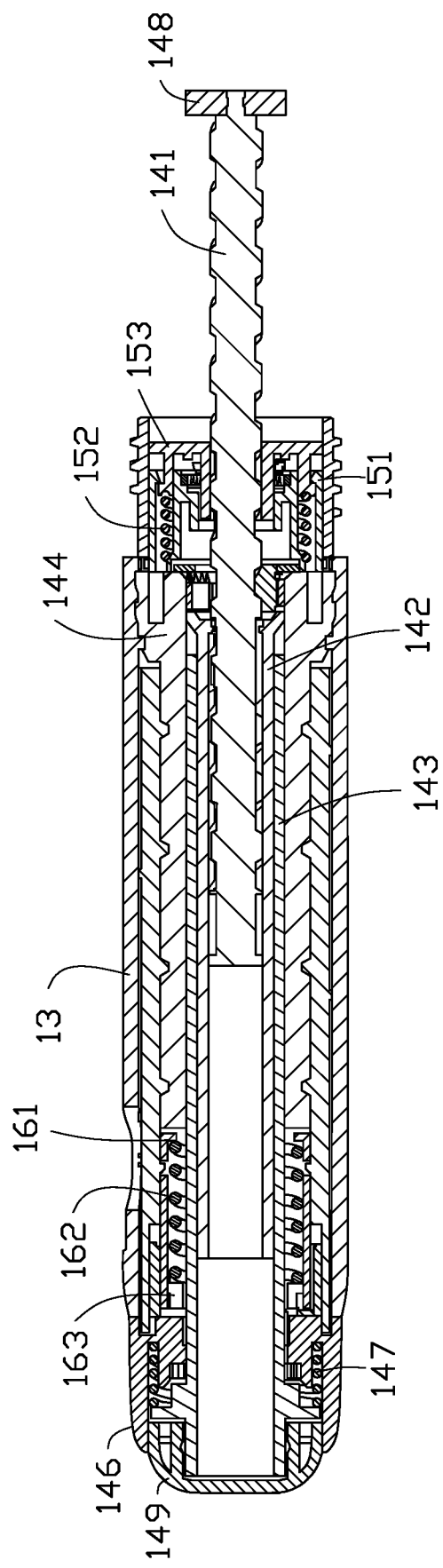
FIG. 19A is a cross-sectional view of a fourth ($4^{th}$) state of the medical injection system, in accordance with an embodiment of the present disclosure.

FIG. 19A is a cross-sectional view of the $4^{th}$ state of the medical injection system 10, in accordance with an embodiment of the present disclosure. When the administration of the drug or the medical fluid is completed, the cartridge 122 is detached from the holder 121 and discarded, and the medical injection system 10 is transformed from the $3^{rd}$ state to the $4^{th}$ state. A section of the lead screw 141 is exposed. In FIG. 19A, the medical injection system 10 is in the $4^{th}$ state: the cartridge 122 is absent therefore is not in contact with the retract nut 153, the retract spring 152 is relaxed, the first interconnecting element 1511 of the locking nut 151 and the second interconnecting element 1533 of the retract nut 153 are disengaged, the relative rotation between the locking nut 151 and the retract nut 153 is possible.

Figure 19B:
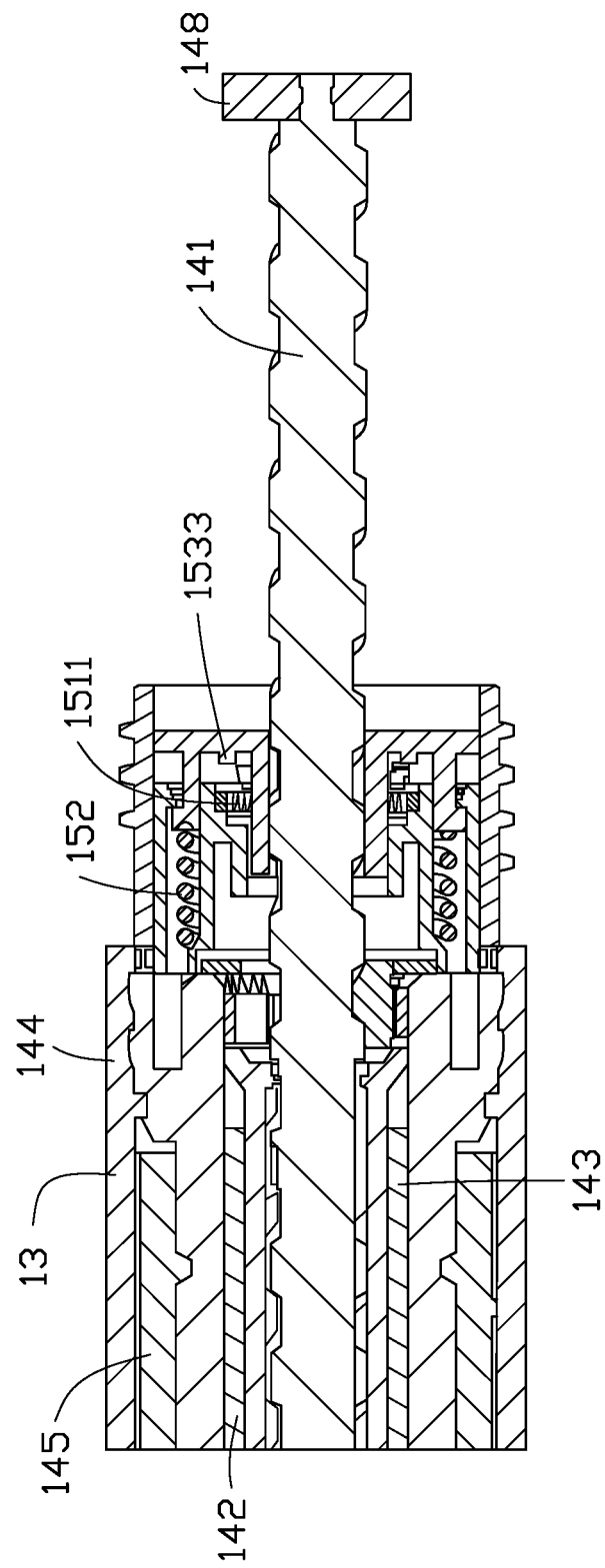
FIG. 19B is another cross-sectional view of the $4^{th}$ state of the medical injection system, in accordance with an embodiment of the present disclosure.

FIG. 19B is a cross-sectional view of a part of the medical injection system 10 in the $4^{th}$ state, in accordance with an embodiment of the present disclosure. The lead screw 141 is coupled to the retract nut 153, therefore the retract nut 153 and the lead screw 141 is also rotatable relative to the locking nut 151. The exposed section of the lead screw 141 can be reduced by pushing the lead screw 141 toward the proximal end. A new cartridge 122 can be loaded into the medical injection system 10 to transform the medical injection system 10 from the $4^{th}$ state into the $1^{st}$ state. The lead screw 141 is pushed toward the proximal end of the medical injection system 10 by the reloading of the new cartridge 122.

The cartridge module 12 is not shown in both FIGS. 19A and 19B. However, the holder 121 can be coupled to the fixed body 144 during the $4^{th}$ state and the cartridge 122 is detached. The holder 121, the cartridge 122, and the stopper 123 can also be simultaneously detached from the medical injection system 10 in the 4th state.

Figure 20:
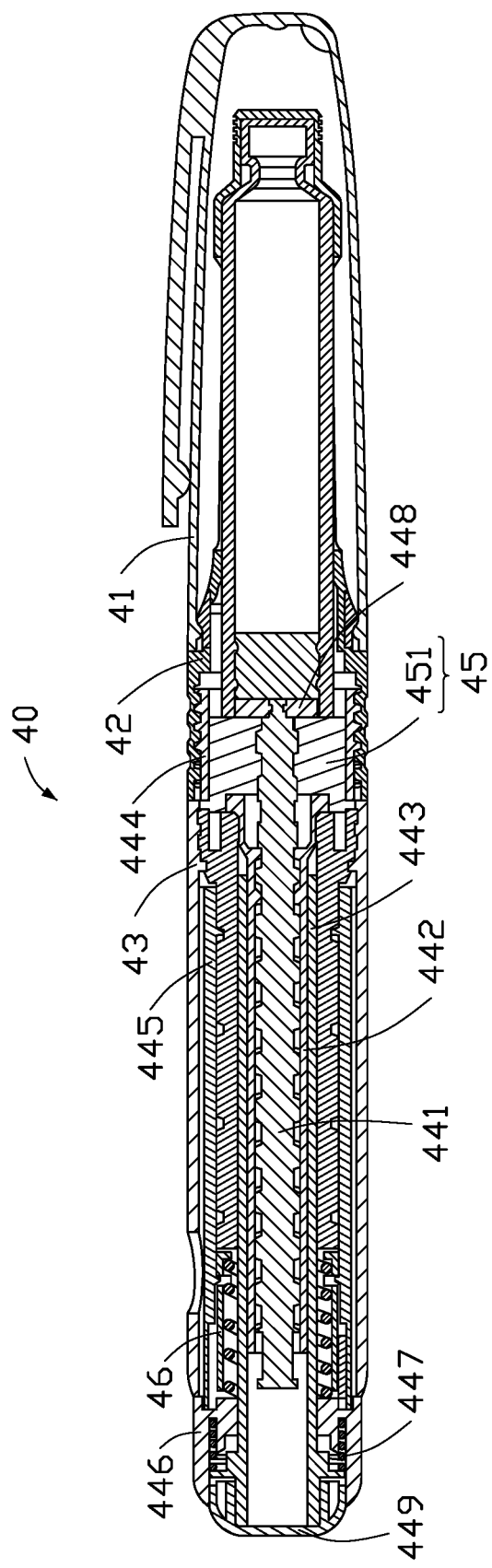
FIG. 20 is a cross-sectional view of a part of another medical injection system, in accordance with an embodiment of the present disclosure.

FIG. 20 is a cross-sectional view of a part of a medical injection system 40, in accordance with an embodiment of the present disclosure. The medical injection system 40 is configured to be used only once. The medical injection system 40 comprises a cap 41, a cartridge module 42, a housing 43, an injection module 44 (not specifically indicated), a retract module 45, and a bi-directional dose setting module 46. The injection module 44 comprises a lead screw 441, a driver 442, a driver sleeve 443, a fixed body 444, a dose indicia 445, a dose knob 446, a button spring 447, a rotation ring 448, and a push button 449. The lead screw 441, the driver 442, the driver sleeve 443, and the dose indicia 445 are assembled concentrically, with the lead screw 441 being the innermost component. A combination of the lead screw 441, the driver 442, the driver sleeve 443, the fixed body 444, the dose indicia 445, the dose knob 446, the button spring 447, the rotation ring 448, and the push button 449 is similar to the combination of respective components in the injection module 14. The retract module 45 is disposed in the fixed body 444, and comprises a retract nut 451.

A $1^{st}$ state of the medical injection system 40 is when the retract nut 451 is in contact with the cartridge module 42, as depicted in FIG. 20. A $2^{nd}$ state of the medical injection system 40 is when the button spring 447 is relaxed, the dose knob 446 is not engaged with the driver sleeve 443. An engagement mechanism between the driver sleeve 443 and the dose knob 446 is similar to the mechanism between the driver sleeve 143 and the dose knob 146. A $3^{rd}$ state of the medical injection system 40 is when the button spring 447 is compressed, the driver sleeve 443 is coupled to the dose knob 446, a rotation of the dose knob 446 drives the driver sleeve 443 to rotate, and the rotation of the driver sleeve 443 drives the driver 442 to rotate. The rotation of the driver 443 causes the lead screw 441 to move axially toward a distal end of the medical injection system 40. The retract module 44 is moved axially toward the distal end. The drug is administered by the medical injection system 40 in the $3^{rd}$ state.

Unlike the medical injection system 10, the medical injection system 40 does not have a 4th state. In the $3^{rd}$ state, the retract module 44 is not capable of returning to its' prior position in the $2^{nd}$ state. The $3^{rd}$ state is a final status of the medical injection system 40, and the medical injection system 40 is discarded after the drug administration.

Figure 21:
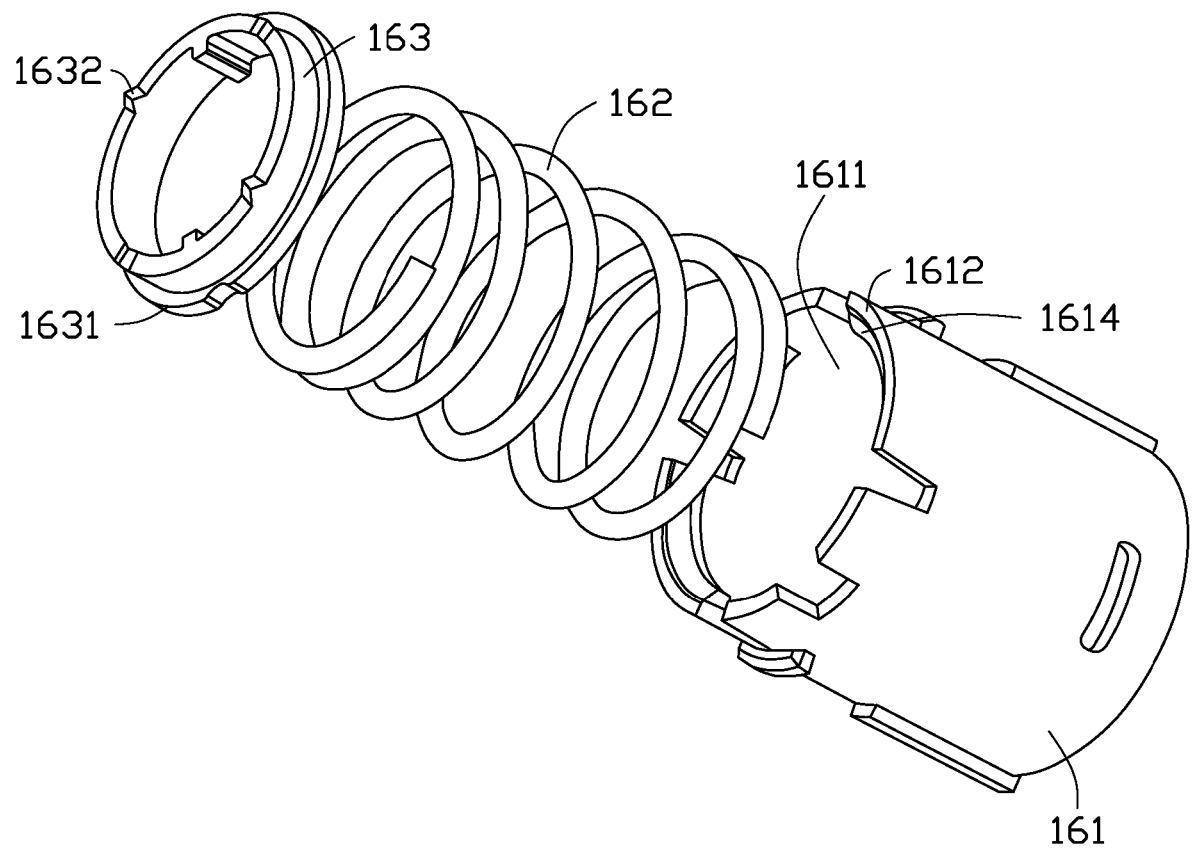
FIG. 21 is an exploded view of a bi-directional dose setting module of the medical injection system, in accordance with an embodiment of the present disclosure.

Another objective of the present disclosure is to generate non-visual responses when adjusting the dose in the medical injection systems. FIG. 21 is an exploded view of a bi-directional dose setting module 16 of the medical injection system 10, in accordance with an embodiment of the present disclosure. The dose plate retainer 161 can be a tube structure having openings on the proximal end and the distal end. The dose plate retainer 161 comprises the lumen 1611 for accommodating the dose spring 162, the proximal flange 1612 facing the proximal end, and a plate coupler 1614 disposed next to the proximal flange 1612. The dose plate 163 can be a ring structure disposed in the lumen 1611 and comprises a retainer coupler 1631 and a fourth teeth 1632. The retainer coupler 1631 is engaged with the plate coupler 1614. The fourth teeth 1632 is engaged with the second teeth 1462 of the dose knob 146.

Figure 22:
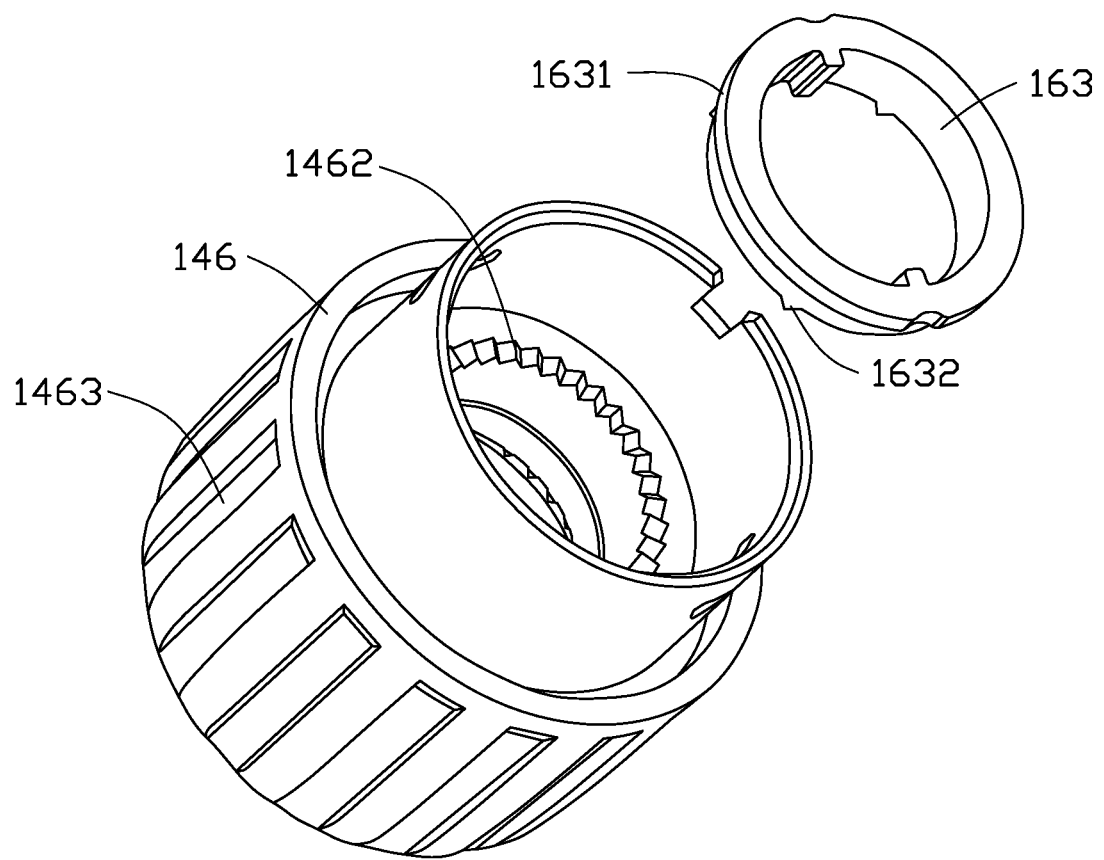
FIG. 22 is an exploded view of a dose plate and a dose knob of the bi-directional dose setting module, in accordance with an embodiment of the present disclosure.

FIG. 22 is an exploded view of the dose plate 163 and the dose knob 146, in accordance with an embodiment of the present disclosure. The dose knob 146 further comprises a knob element 1463 suitable for the user to hold and rotate.

The second teeth 1462 of the dose knob 146 is facing the distal end and the fourth teeth 1632 of the dose plate 163 is facing the proximal end, and the second teeth 1462 of the dose knob 146 is engaged with the fourth teeth 1632. The bi-directional dose setting module 16 is capable to generate different responses when the fourth teeth 1632 are rotated relative to the second teeth 1462. When the dose knob 146 is rotated in the $1^{st}$ direction, the second teeth 1462 is rotated relative to the fourth teeth 1632 and generates a $1^{st}$ response. When the dose knob 146 is rotated in the $2^{nd}$ direction, the second teeth 1462 is rotated relative to the fourth teeth 1632 and generates a $2^{nd}$ response. The $1^{st}$ response can be a $1^{st}$ click sound to inform the user that the dose of the drug or the medical fluid is increased in the medical injection system 10. Because the dose knob 146 is coupled to the dose indicia 145, the $2^{nd}$ response can be a $2^{nd}$ click sound to inform the user that the dose of the drug or the medical fluid is decreased in the medical injection system 10. The $1^{st}$ click sound and the $2^{nd}$ click sound are convenient indications for the user to adjust the dose.

Figure 23:
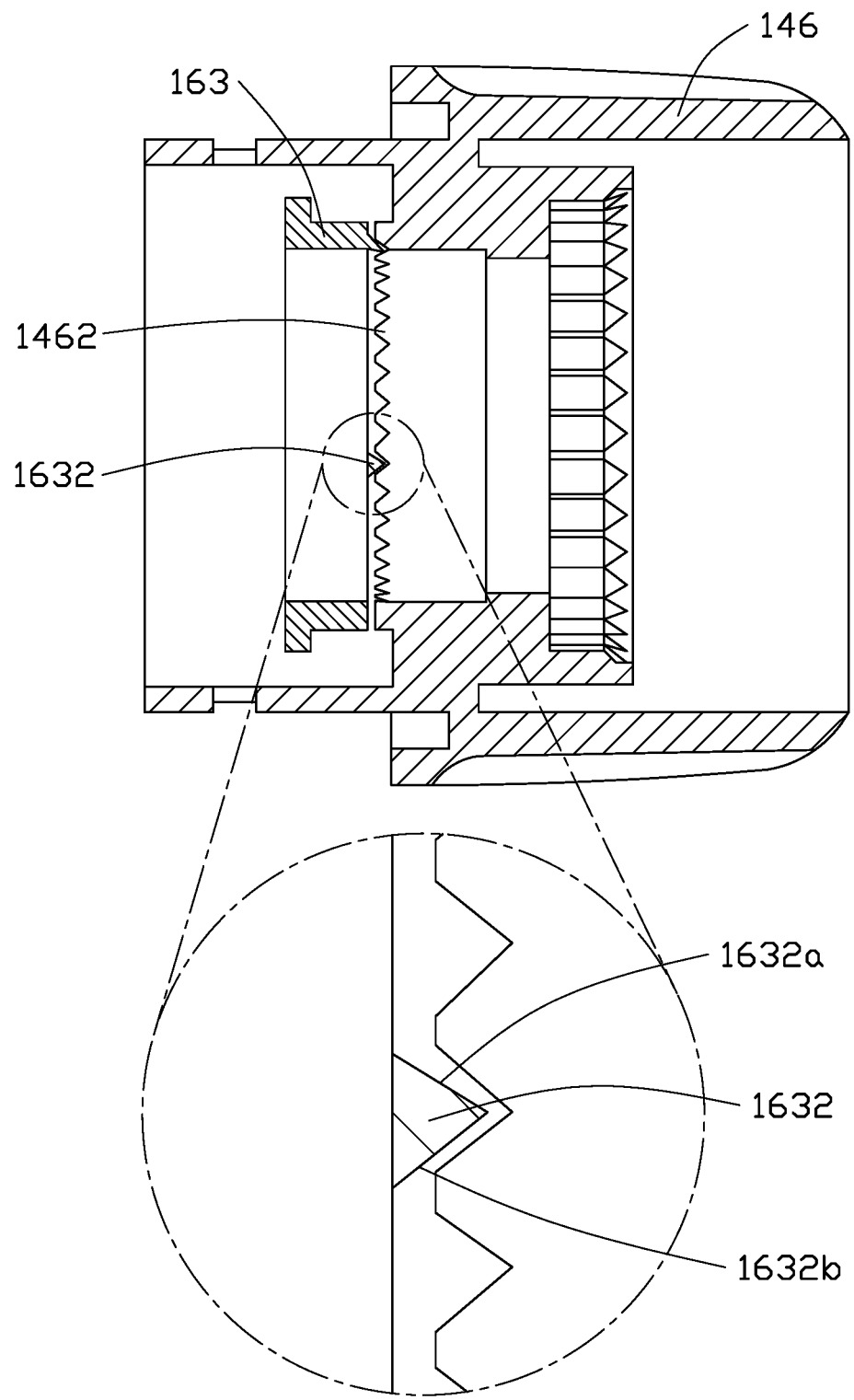
FIG. 23 is a cross-sectional view of a combination of the dose plate and the dose knob, in accordance with an embodiment of the present disclosure.
Figure 24:
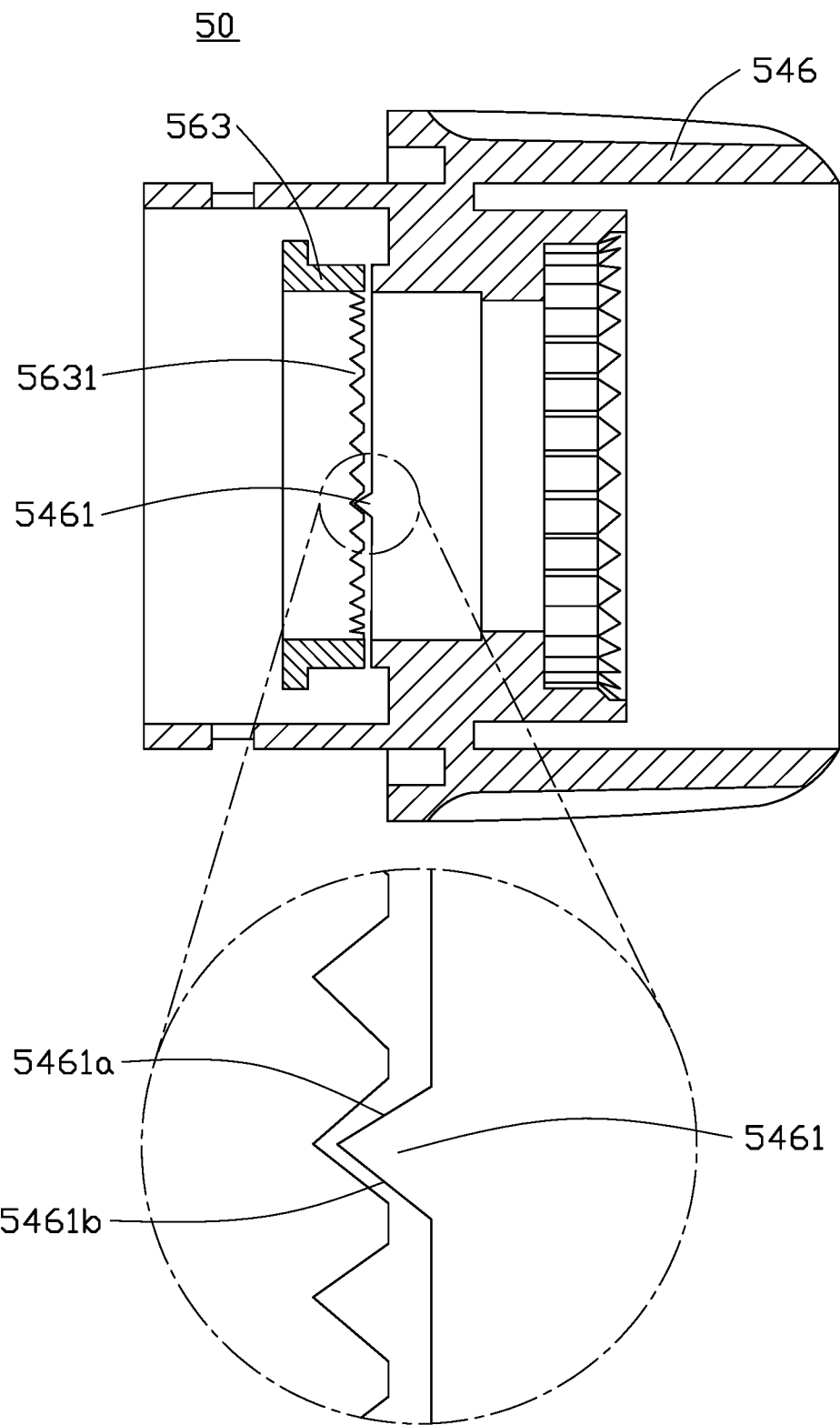
FIG. 24 is a cross-sectional view of a combination of another dose plate and another dose knob, in accordance with an embodiment of the present disclosure.

Mechanisms for generating the $1^{st}$ response and the $2^{nd}$ response are illustrated in detail in FIGS. 23 and 24. In contrast with previous figures, in FIGS. 23 and 24, a proximal direction of the medical injection system is on a right side of the figure, and a distal direction of the medical injection system is on a left side of the figure. FIG. 23 is an enlarged cross-sectional view of a combination of the dose plate 163 and the dose knob 146, in accordance with an embodiment of the present disclosure. In FIG. 23, an amount of the second teeth 1462 is larger than an amount of the fourth teeth 1632. Each of the tooth in the fourth teeth 1632 comprises a first slope 1632a and a second slope 1632b. The second slope 1632b is steeper than the first slope 1632a. When one of the second teeth 1462 moves over the first slope 1632a, the $1^{st}$ response is generated in the form of the $1^{st}$ click sound. When one of the second teeth 1462 moves over the second slope, the $2^{nd}$ response is generated in the form of the $2^{nd}$ click sound. When the dose knob 146 is rotated, the user would be able to recognize the direction of the rotation upon hearing the $1^{st}$ click sound and the $2^{nd}$ click sound, thereby adjusting the dose. The first slope 1632a can also be steeper than the second slope 1632b.

FIG. 24 is an enlarged cross-sectional view of another dose knob 546 and another dose plate 563, in accordance with an embodiment of the present disclosure. The dose knob 546 can be rotated by the user to adjust the dose of the drug to be administered by another medical injection system 50 (not fully shown). The dose knob 546 comprises a second teeth 4461 facing a distal end of the medical injection system 50. The dose plate 563 comprises a fourth teeth 5631 facing a proximal end of the medical injection system 50, and the fourth teeth 5631 is engaging with the second teeth 5461. In FIG. 24, an amount of the second teeth 5461 is smaller than an amount of the fourth teeth 5631. Each of the tooth in the second teeth 5461 comprises a first slope 5461a and a second slope 5461b. The second slope 5461b is steeper than the first slope 5461a. When one of the fourth teeth 5631 moves over the first slope 5461a, the $1^{st}$ response is generated in the form of the $1^{st}$ click sound. When one of the fourth teeth 5631 moves over the second slope, the $2^{nd}$ response is generated in the form of the $2^{nd}$ click sound. When the dose knob 546 is rotated, the user would be able to recognize the direction of the rotation upon hearing the $1^{st}$ click sound and the $2^{nd}$ click sound, thereby adjusting the dose. The first slope 5461a can also be steeper than the second slope 4461b.

The embodiments shown and described above are only examples. Many details are often found in the art. Therefore, many such details are neither shown nor described. Even though numerous characteristics and advantages of the present disclosure have been set forth in the foregoing description, together with details of the structure and function of the present disclosure, the present disclosure is illustrative only, and changes may be made in the detail. It will therefore be appreciated that the embodiment described above may be modified within the scope of the claims.

What is claimed is:

1. A medical injection system, comprising:
an injection module, comprising:
  a lead screw movable in an axial direction of the medical injection system;
  a driver rotatable in a first direction and accommodating the lead screw, the driver comprising a resilient flange and a first engaging element, the first engaging element being on an external surface of the driver, and a shape of the driver being not identical to a shape of the lead screw along a transverse plane of the medical injection system;
  a fixed body comprising a ratchet and a first helical element, the ratchet coupled to the resilient flange of the driver for preventing the driver from rotating in a second direction, and the first helical element being on an external surface of the fixed body;
  a dose indicia rotatable in the first direction and the second direction, the dose indicia comprising a plurality of marks and a second helical element, the plurality of marks being on an external surface of the dose indicia, and the second helical element being on the internal surface of the dose indicia for coupling to the first helical element of the fixed body;
  a dose knob rotatable in the first direction and the second direction and coupled to a proximal end of the dose indicia, the dose knob comprising a plurality of first teeth and a plurality of second teeth, the plurality of first teeth circumferentially disposed on an internal surface of the dose knob, and the second plurality of teeth facing a distal end of the medical injection system;
  a driver sleeve rotatable in the first direction and the second direction and partially accommodated by the fixed body, the driver sleeve partially accommodating the driver and comprising a second engaging element and a plurality of third teeth, the second engaging element being on an internal surface of the driver sleeve for coupling to the first engaging element of the driver, and the plurality of third teeth being capable of engaging with the plurality of first teeth of the dose knob;
  a button spring disposed between the dose knob and the driver sleeve;
  a retract module accommodated by the fixed body of the injection module; and
  a bi-directional dose setting module, comprising:
  a dose plate retainer accommodated by the dose indicia of the injection module and comprising a lumen, a plate coupler, a proximal flange, and a distal flange, the proximal flange facing a proximal end of the medical injection system, and the distal flange facing the distal end of the medical injection system;
  a dose plate comprising a retainer coupler and a plurality of fourth teeth, the retainer coupler coupled to the plate coupler, and the plurality of fourth teeth engaged with the plurality of second teeth of the dose knob; and
  a dose spring disposed in the lumen and contacting the distal flange of the dose plate, wherein:
  when the dose knob is rotated in the first direction, the plurality of second teeth is rotated relative to the plurality of fourth teeth and a first response is generated; and
  when the dose knob is rotated in the second direction, the plurality of second teeth is rotated relative to the plurality of fourth teeth and a second response is generated.

2. The medical injection system of claim 1, wherein:
an amount of the plurality of second teeth is larger than an amount of the plurality of fourth teeth;
each of the plurality of fourth teeth comprises a first slope and a second slope;
the first response is generated by the plurality of second teeth moving over the first slope; and
the second response is generated by the plurality of second teeth moving over the second slope.

3. The medical injection system of claim 1, wherein:
an amount of the plurality of second teeth is smaller than an amount of the plurality of fourth teeth;
each of the plurality of fourth teeth comprises a first slope and a second slope;
the first response is generated by the plurality of second teeth moving over the first slope; and
the second response is generated by the plurality of second teeth moving over the second slope.

4. The medical injection system of claim 1, further comprising a housing for accommodating the dose indicia, the housing comprising a window for exposing at least one of the plurality of marks of the dose indicia.

5. The medical injection system of claim 1, further comprising a cartridge module coupled to the fixed body of the injection module.

6. The medical injection system of claim 5, further comprising a cap detachably coupled to the cartridge module.

7. The medical injection system of claim 5, wherein:
the medical injection system is operably configured to transform between a first state, a second state, and a third state;
in the first state, the cartridge module is in contact with a retract nut of the retract module;
in the second state, the button spring is relaxed, the plurality of first teeth is not engaged with the plurality of third teeth, and the driver sleeve is not rotated by a rotation of the dose knob; and
in the third state, the button spring is compressed, the plurality of first teeth is engaged with the plurality of third teeth, the dose knob is rotated, the rotation of the dose knob drives the driver sleeve to rotate, the rotation of the driver sleeve drives the driver to rotate, and the rotation of the driver causes the lead screw to move axially toward the distal end of the medical injection system.

8. The medical injection system of claim 7, wherein:
the injection module further comprises a push button disposed on the proximal end of the medical injection system and coupled to the driver sleeve; and
when the push button is pressed, the medical injection system is transformed from the second state to the third state.

9. The medical injection system of claim 7, wherein the cartridge module comprises a stopper capable of being pushed by the lead screw when the lead screw is moved axially toward the distal end of the medical injection system.

10. The medical injection system of claim 1, further comprising a cartridge module, the cartridge module comprising a holder and a cartridge, the holder coupled to the fixed body of the injection module, and the cartridge detachably coupled to the holder.

11. The medical injection system of claim 10, wherein:
the retract module comprises a locking nut and a retract spring;
the locking nut comprises a first interconnecting element facing the distal end of the medical injection system;
the retract spring is disposed between the locking nut and a retract nut; and
the retract nut comprises a second interconnecting element facing the proximal end of the medical injection system.

12. The medical injection system of claim 11, wherein the locking nut further comprises a circular groove, and the retract spring is partially accommodated by the circular groove.

13. The medical injection system of claim 11, wherein the retract nut further comprises a circular groove, and the retract spring is partially accommodated by the circular groove.

14. The medical injection system of claim 11, wherein:
the medical injection system is operably configured to transform between a first state, a second state, a third state, and a fourth state;
in the first state, the cartridge is in contact with the retract nut;
in the second state, the button spring is relaxed, the plurality of first teeth is not engaged with the plurality of third teeth, and the driver sleeve is not rotated by a rotation of the dose knob;
in the third state, the button spring is compressed, the plurality of first teeth is engaged with the plurality of third teeth, the dose knob is rotated, the rotation of the dose knob drives the driver sleeve to rotate, the rotation of the driver sleeve drives the driver to rotate, and the rotation of the driver causes the lead screw to move axially toward the distal end of the medical injection system; and
in the fourth state, the cartridge is not in contact with the retract nut and the lead screw is moved axially toward the proximal end of the medical injection system.

15. The medical injection system of claim 14, wherein:
when the medical injection system is in the first state, the retract spring is compressed, and the first interconnecting element and the second interconnecting element are engaged; and
when the medical injection system is in the fourth state, the retract spring is relaxed, and the first interconnecting element and the second interconnecting element are not engaged.

16. The medical injection system of claim 14, wherein the injection module further comprises a push button disposed on the proximal end of the medical injection system and coupled to the driver sleeve, and when the push button is pressed, the medical injection system is transformed from the second state to the third state.

17. A medical injection system, comprising:
an injection module, comprising:
a lead screw movable in an axial direction of the medical injection system;
a driver rotatable in a first direction and accommodating the lead screw, the driver comprising a resilient flange and a first engaging element, the first engaging element being on an external surface of the driver, and a shape of the driver being not identical to a shape of the lead screw along a transverse plane of the medical injection system;
a fixed body comprising a ratchet and a first helical element, the ratchet coupled to the resilient flange of the driver for preventing the driver from rotating in a second direction, and the first helical element being on an external surface of the fixed body;
a dose adjustment element rotatable in the first direction and the second direction, the dose adjustment element comprising a plurality of marks, a second helical element, and a knob part, the plurality of marks being on an external surface of the dose adjustment element, the second helical element being on the internal surface of the dose adjustment element for coupling to the first helical element of the fixed body, the knob part being on a proximal end of the dose adjustment element and comprising a plurality of first teeth and a plurality of second teeth, the plurality of first teeth circumferentially disposed in an internal surface of the knob part, and the plurality of second teeth facing a distal end of the medical injection system;
a driver sleeve rotatable in the first direction and the second direction and partially accommodated by the fixed body, the driver sleeve partially accommodating the driver and comprising a second engaging element and a plurality of third teeth, the second engaging element being on an internal surface of the driver sleeve for coupling to the first engaging element of the driver, and the plurality of third teeth being capable of engaging with the plurality of first teeth of the knob;
a button spring disposed between the dose knob and the driver sleeve;
a retract module accommodated by the fixed body of the injection module; and
a bi-directional dose setting module, comprising:
a dose plate retainer accommodated by a dose indicia of the injection module and comprising a lumen, a plate coupler, a proximal flange, and a distal flange, the proximal flange facing a proximal end of the medical injection system, and the distal flange facing the distal end of the medical injection system;
a dose plate comprising a retainer coupler and a plurality of fourth teeth, the retainer coupler coupled to the plate coupler, and the plurality of fourth teeth engaged with the plurality of second teeth of the knob part; and
a dose spring disposed in the lumen and contacting the distal flange of the dose plate, wherein:
when the knob part is rotated in the first direction, the plurality of second teeth is rotated relative to the plurality of fourth teeth and a first response is generated; and
when the knob part is rotated in the second direction, the plurality of second teeth is rotated relative to the plurality of fourth teeth and a second response is generated.

* * * * *